US 12,053,765 B2

United States Patent
Li et al.

(10) Patent No.: US 12,053,765 B2
(45) Date of Patent: Aug. 6, 2024

(54) SELECTIVE CARBON DIOXIDE REDUCTION CATALYZED BY SINGLE METAL SITES ON CARBON NITRIDE UNDER VISIBLE LIGHT IRRADIATION

(71) Applicant: University of New Hampshire, Durham, NH (US)

(72) Inventors: Gonghu Li, Newmarket, NH (US); Anatoly Frenkel, Great Neck, NY (US); Peipei Huang, Dover, NH (US); Jiahao Huang, Port Jefferson, NY (US)

(73) Assignees: University of New Hampshire, Durham, NH (US); The Research Foundation for The State University of New York, Albany, NY (US)

( * ) Notice: Subject to any disclaimer, the term of this patent is extended or adjusted under 35 U.S.C. 154(b) by 295 days.

(21) Appl. No.: 16/891,442

(22) Filed: Jun. 3, 2020

(65) Prior Publication Data
US 2020/0376475 A1    Dec. 3, 2020

Related U.S. Application Data

(60) Provisional application No. 62/856,443, filed on Jun. 3, 2019.

(51) Int. Cl.
*B01J 31/18* (2006.01)
*B01J 35/39* (2024.01)
(Continued)

(52) U.S. Cl.
CPC ........... *B01J 31/1815* (2013.01); *B01J 35/39* (2024.01); *B01J 37/04* (2013.01); *C01B 32/40* (2017.08);
(Continued)

(58) Field of Classification Search
None
See application file for complete search history.

(56) References Cited

FOREIGN PATENT DOCUMENTS

| CN | 105713030 A | 6/2016 |
|---|---|---|
| CN | 105749914 A | 7/2016 |

(Continued)

OTHER PUBLICATIONS

Huang et al., Selective CO2 reduction catalyzed by single cobalt sites on carbon nitride under visible-light irradiation, J. Am. Chem. Soc., 2018, 16042-16047 (Year: 2018).*

(Continued)

*Primary Examiner* — Sheng H Davis
*Assistant Examiner* — Keling Zhang
(74) *Attorney, Agent, or Firm* — Finch & Maloney PLLC

(57) ABSTRACT

A composition of a photocatalyst, a method of manufacturing the photocatalyst, and a method of chemically reducing carbon dioxide to carbon monoxide using the photocatalyst under visible-light irradiation is provided. The photocatalyst comprises a transition metal ion and graphitic carbon nitride and includes single metal sites on carbon nitride. Under visible light, the metal sites that are coordinated to nitrogen atoms get activated, without the use of additional ligands, to catalyze the reduction of carbon dioxide to selectively produce carbon monoxide. The photocatalytic reduction of carbon dioxide to carbon monoxide is highly efficient, resulting a turnover number of more than 800 for carbon monoxide production in 2 hours. The composition is useful in converting carbon dioxide into useful chemicals and carbon-based fuels. A functional model of molecular catalysts for efficient carbon dioxide reduction is also present.

10 Claims, 26 Drawing Sheets

(51) Int. Cl.
  *B01J 37/04* (2006.01)
  *C01B 32/40* (2017.01)
  *C07D 487/16* (2006.01)
(52) U.S. Cl.
  CPC ....... *C07D 487/16* (2013.01); *B01J 2231/005* (2013.01); *B01J 2231/625* (2013.01); *B01J 2531/845* (2013.01)

(56) References Cited

FOREIGN PATENT DOCUMENTS

| CN | 105983420 A | 10/2016 |
|---|---|---|
| CN | 108855187 A | 11/2018 |
| JP | 2009275033 A | 11/2009 |
| JP | 2015048351 A | 3/2015 |
| WO | 2020046064 A1 | 3/2020 |

OTHER PUBLICATIONS

Mu et al., Cobalt-doped graphitic carbon nitride with enhanced peroxide-like activity for wastewater treatment, RSC Adv., 2016, 6, 35568 (Year: 2016).*

Li et al., Synthesis of carbon-doped g—C3N4 composites with enhanced visible-light photocatalytic activity, Materials Letters, 2014, 137, 281-284 (Year: 2014).*

"Proceedings of the Fortieth DOE Solar Photochemistry P.I. Meeting," Chemical Sciences, Geosciences, and Biosciences Division Office of Basic Energy Sciences—Office of Science—U.S. Department of Energy. Jun. 4-7, 2018. 162 pages.

Zhang, et al., "Ultrafine Cobalt Catalysts on Covalent Carbon Nitride Frameworks for Oxygenic Photosynthesis," Applied Materials & Interfaces (ACS) Research Article, published Jan. 5, 2016. pp. 2287-2296.

Gao, et al., "Heterogeneous Single-Atom Catalyst for Visible-Light-Driven High-Turnover CO2 Reduction: The Role of Electron Transfer," Advanced Materials, 2018, vol. 30, 1704624. 9 pages.

Huang, et al., "Selective CO2 Reduction Catalyzed by Single Cobalt Sites on Carbon Nitride under Visible-Light Irradiation," Journal of The American Chemical Society, Published Nov. 10, 2018, vol. 140, pp. 16042-16047.

Wang, et al., "Recent Advances of Graphitic Carbon Nitride-Based Structures and Applications in Catalyst, Sensing, Imaging, and LEDs," CrossMark, Nano-Micro Lett. (2017) 9:47. 21 pages.

Won, et al., "Highly Robust Hybrid Photocatalyst for Carbon Dioxide Reduction: Tuning and Optimization of Catalytic Activities of Dye/TiO2/Re(I) Organic-Inorganic Ternary Systems," ACS Publications, Journal of The American Chemical Society, Published-Oct. 10, 2015, vol. 137. pp. 13679-13690.

Adachi, et al., "Photocatalytic Reduction of Carbon Dioxide to Hydrocarbon Using Copper-Loaded Titanium Dioxide," Solar Energy, vol. 53, No. 2, 1994. pp. 187-190.

Bonin, et al., "Selective and Efficient Photocatalytic CO2 Reduction to CO Using Visible Light and an Iron-Based Homogeneous Catalyst," Journal of The American Chemical Society, Nov. 14, 2014. pp. 16768-16771.

Kumar, et al., "Cobalt Phthalocyanine Immobilized on Graphene Oxide: An Efficient Visible-Active Catalyst for the Photoreduction of Carbon Dioxide," Chemistry, A European Journal, 2014. pp. 6154-6161.

Lehn, Jean-Marie and Ziessel, Raymond, "Photochemical generation of carbon monoxide and hydrogen by reduction of carbon dioxide and water under visible light irradiation," Proc. Natl. Acad. Sci. USA, vol. 79, Jan. 1982. pp. 701-704.

Morris, et al., "Molecular Approaches to the Photocatalytic Reduction of Carbon Dioxide for Solar Fuels," Accounts of chemical research, vol. 42, No. 12, Dec. 2009. pp. 1983-1994.

Pan, Pei-Wen and Chen, Yu-Wen, "Photocatalytic reduction of carbon dioxide on NiO/InTaO4 under visible light Irradiation," Elsevier, Catalysis Communications, vol. 8, 2007. pp. 1546-1549.

Sastre, et al., "Complete Photocatalytic Reduction of CO2 to Methane by H2 under Solar Light Irradiation," Journal of The American Chemical Society, Apr. 11, 2014. pp. 6798-6801.

Tinnemans, et al., Tetraaza-macrocyclic cobalt (II) and nickle (II) complexes as electron-transfer agents in the photo (electro) chemical and electrochemical reduction of carbon dioxide, Institute of Applied Chemistry, Mar. 14, 1984. 8 pages.

Wang, et al., "Doping MetalOrganic Frameworks for Water Oxidation, Carbon Dioxide Reduction, and Organic Photocatalysis," Journal of The American Chemical Society, Jul. 22, 2011. pp. 13445-13454.

Zhang, et al., "Efficient Visible-Light-Driven Carbon Dioxide Reduction by a Single-Atom Implanted Metal-Organic Framework," Angew. Chem Int. Ed. 2016, vol. 55. pp. 14310-14314.

Zhao, et al., "Photo-catalytic reduction of carbon dioxide with in-situ synthesized CoPc/TiO2 under visible light Irradiation," Elsevier, Journal of Cleaner Production, vol. 17, 2009. pp. 1025-1029.

* cited by examiner

FIG. 8A-F

SELECTIVE CARBON DIOXIDE REDUCTION CATALYZED BY SINGLE METAL SITES ON CARBON NITRIDE UNDER VISIBLE LIGHT IRRADIATION

CROSS REFERENCE TO RELATED APPLICATIONS

This application claims the benefit of U.S. Provisional Application No. 62/856,443, filed Jun. 3, 2019, the disclosure of which is incorporated by reference herein in its entirety.

GOVERNMENT FUNDED RESEARCH

This invention was made with government support under DE-SC0012335, DE-SC0016417, DE-FG02-03ER15476, and DE-SC0012704 awarded by the U.S. Department of Energy, and CBET1510810 awarded by the National Science Foundation. The government has certain rights in the invention.

FIELD OF THE DISCLOSURE

The present disclosure relates generally to photocatalysts made of earth-abundant elements and, in particular, to photocatalysts for reducing carbon dioxide into energy-rich fuels under visible light.

BACKGROUND

A photocatalyst is a material that absorbs light to pump electrons to a higher energy level and subsequently transfers electrons to facilitate a chemical reaction to occur. In many chemical reactions, metal-ligand complexes have been used as catalysts. However, they are often expensive and difficult to prepare.

SUMMARY

In one aspect, a photocatalyst is provided. The photocatalyst may include a graphitic carbon nitride coordinated with atomically dispersed $Co^{n+}$ in absence of additional ligands. The $Co^{n+}$ may form coordinate bonds with nitrogen atoms in the graphitic carbon nitride where the nitrogen atoms may maintain a flat framework and may form a plane within the graphitic carbon nitride. The $Co^{n+}$ may be positioned outside the plane. In one embodiment, $Co^{n+}$ may be $Co^{2+}$. $Co^{2+}$ may be present in any effective amount, for example, at a concentration between 0.004 and 0.430 μmol/mg of the photocatalyst. $Co^{2+}$ may be uniformly distributed on the graphitic carbon nitride. The molar ratio of $Co^{2+}$ to cobalt oxide in the photocatalyst may be greater than 1000. The graphitic carbon nitride may be planar and may also include carbon doping. $Co^{n+}$ may be off the plane formed by the nitrogen atoms by a distance less than 0.5 Angstrom. $Co^{n+}$ may form coordinate bonds with four nitrogen atoms on the graphitic carbon nitride. The photocatalyst may include earth-abundant elements.

In another aspect, a method for manufacturing a photocatalyst is provided. The method includes preparing a mixture of graphitic carbon nitride and a cobalt salt in a polar solvent and forming a $Co^{n+}$-carbon nitride complex. The $Co^{n+}$-carbon nitride complex may include a graphitic carbon nitride having single metal sites that may be directly coordinated with $Co^{n+}$, and $Co^{n+}$ may form coordinate bonds with nitrogen atoms in the graphitic carbon nitride. The nitrogen atoms may maintain a flat framework and may form a plane within the graphitic carbon nitride. The $Co^{n+}$ may be positioned outside the plane. The graphitic carbon nitride may include carbon doping. In one embodiment, $Co^{n+}$ is $Co^{2+}$. The complex may have a $Co^{2+}$ concentration between 0.004 and 0.430 μmol/mg of the complex. The mixture may further include triethylamine. The polar solvent may include acetonitrile. The polar solvent may include a volume ratio of acetonitrile to triethylamine of from 100:1 to 150:1. The cobalt salt may include a cobalt halide. The cobalt salt may be a cobalt dichloride. The method for manufacturing the photocatalyst may include heating the mixture and heating may include using microwave radiation. The mixture may be heated to at least 80° C. for at least 2 hours. The method may also include stirring in presence of a dispersant. The method may further include using X-ray absorption spectroscopy to confirm a single metal ion site structure.

In another aspect, a method for chemically reducing carbon dioxide is provided. The method may include dispersing a photocatalyst in a polar solvent, and the photocatalyst may include a graphitic carbon nitride including single metal sites directly coordinated with metal ions. The method may also include introducing carbon dioxide to the dispersion to provide a carbon dioxide containing dispersion, irradiating the carbon dioxide containing dispersion with visible light, and reducing at least some of the carbon dioxide to carbon monoxide. The dispersion may include an electron donor. The electron donor may be triethanolamine. The polar solvent may be acetonitrile. The dispersion may include a volume ratio of acetonitrile to triethanolamine of from 2:1 to 10:1. The graphitic carbon nitride may include carbon doping. The nitrogen atoms in the carbon nitride may maintain a flat framework in a plane and the metal ions may form coordinative bonds with the nitrogen atoms and are positioned outside the plane. The metal ions may be transition metal ions. In some embodiments, the metal ions may be cobalt ions. In one embodiment, the metal ions may be $Co^{2+}$, and $Co^{2+}$ may be off the plane formed by the nitrogen atoms by a distance less than 0.5 Angstrom. $Co^{2+}$ may be present at a concentration between 0.004 and 0.430 μmol/mg of graphitic carbon nitride. The photocatalyst may reduce carbon dioxide to yield carbon monoxide. In the method, visible light may be provided by solar radiation or by a halogen lamp. Visible light may include photons with wavelengths between 350 nm and 800 nm. In some embodiments, visible light may contain photons with wavelengths between 420 nm and 650 nm. The method may also include recycling the photocatalyst. The morphology of the photocatalyst may remain unchanged after recycling the photocatalyst. Carbon dioxide may be selectively reduced to CO with a turnover number of carbon monoxide between 1 and 250, where the turnover number is a ratio of moles of carbon monoxide to moles of cobalt.

BRIEF DESCRIPTION OF THE DRAWINGS

(FIG. 21A) before, and (FIG. 21B) after photocatalysis for 30 h. (FIG. 21C) before and (FIG. 21D) after photocatalysis for five 2-hour cycles.

Various aspects of at least one example are discussed below with reference to the accompanying figure, which is not intended to be drawn to scale. The figure is included to provide an illustration and a further understanding of the various aspects and examples, and are incorporated in and constitute a part of this specification, but are not intended to limit the scope of the disclosure. The drawings, together with the remainder of the specification, serve to explain principles and operations of the described and claimed aspects and examples. For purposes of clarity, not every component may be labeled in every figure.

GENERAL OVERVIEW

Described herein is a graphitic carbon nitride including single metal sites that form coordinate bonds with transition metal ions ($M^{n+}$). These carbon nitride transition metal structures are hereafter referred to as $M^{n+}$—$C_3N_4$. In $M^{n+}$—$C_3N_4$, the graphitic carbon nitride can include single metal sites forming coordinate bonds with transition metal ions in absence of any additional ligands. The $M^{n+}$—$C_3N_4$ is capable of catalyzing the photoreduction of $CO_2$ under visible light. $M^{n+}$—$C_3N_4$ reduces $CO_2$ to yield CO in the presence of an electron donor. $M^{n+}$—$C_3N_4$ is highly active and selectively reduces $CO_2$ to CO. In one set of embodiments, the transition metal ion can be $Co^{n+}$. In specific embodiments, $Co^{n+}$ can be $Co^{2+}$. $Co^{2+}$ can form co-ordinate bonds with nitrogen atoms in the graphitic carbon nitride to form $Co^{2+}$—$C_3N_4$ that includes single metal sites. The $Co^{2+}$—$C_3N_4$ is an efficient photocatalyst under visible-light irradiation and can exhibit a turnover number, the ratio of moles of CO produced to moles of $Co^{2+}$ in the photocatalyst, of more than 800 after photocatalysis for 2 hours.

DETAILED DESCRIPTION

Figure 1A:
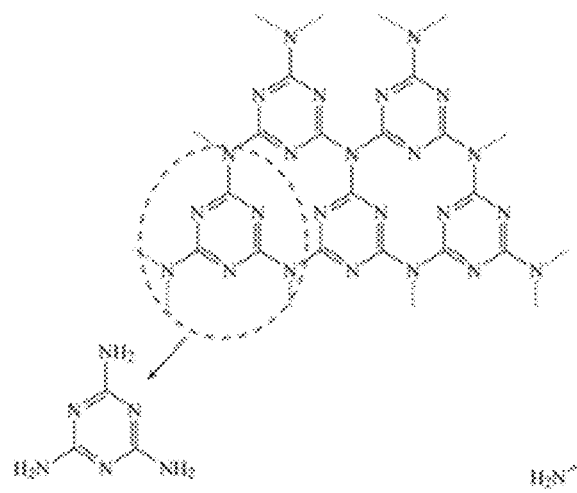
FIG. 1A illustrates a triazine structure of graphitic carbon nitride ($C_3N_4$)
Figure 1B:
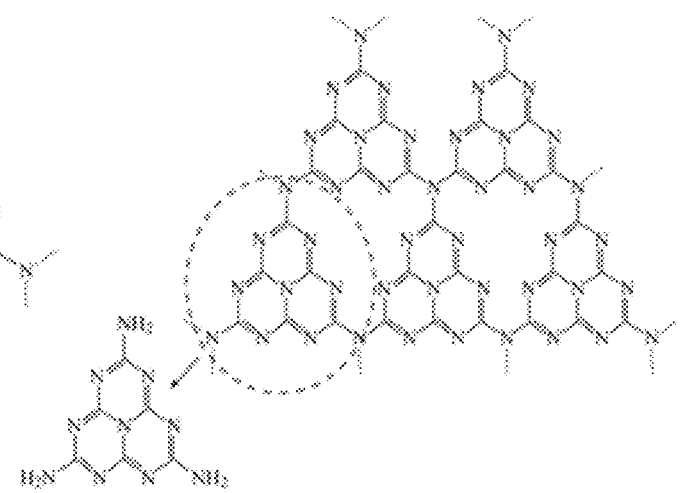
FIG. 1B illustrates a heptazine structure of $C_3N_4$.

Carbon nitrides are compounds of carbon and nitrogen. They are covalent network compounds that include beta carbon nitrides and graphitic carbon nitride. They may be void of other elements or void of other elements except for hydrogen. The beta carbon nitrides are solids with a formula β-$C_3N_4$, and can have a hardness of greater than that of diamond. Graphitic carbon nitrides are also solids and have a formula g-$C_3N_4$, or simply $C_3N_4$. It can have two major substructures based on triazine units, as shown in FIG. 1A, and heptazine units, as shown in FIG. 1i, which, depending on reaction conditions, exhibit different degrees of condensation, different properties and varied reactivities.

The structure of $C_3N_4$, in general, is similar to that of graphene, but with a carbon lattice that has been partially substituted with nitrogen atoms in a regular fashion. The structure of $C_3N_4$, in general, is planar. However, in some embodiments, $C_3N_4$ structure can include planar sheets, or corrugated sheets, or both. In some embodiments, $C_3N_4$ can be fully polymerized. In some other embodiments, $C_3N_4$ can be partially polymerized. Synthesized $C_3N_4$ materials typically contain hydrogen atoms. The polymeric $C_3N_4$ structure can be highly ordered, with some hydrogen atoms at the edges of $C_3N_4$ flakes, in the forms of $-NH_2$ and $-OH$ groups.

$C_3N_4$ can be prepared by several different methods including by polymerization of cyanamide, dicyandiamide or melamine. In one set of embodiments, $C_3N_4$ can be prepared by pyrolysis of urea. In particular, a desired amount of urea can be calcined in a muffle furnace at 600° C. for 4 hours (with a ramp rate 5° C./min) to prepare $C_3N_4$.

The calcination temperature and its duration can also vary. In some embodiments, $C_3N_4$ can be prepared by calcining urea in a muffle furnace at a temperature less than 1000° C., less than 800° C. or less than 700° C. In some other embodiments, $C_3N_4$ can be prepared by calcining urea in a muffle furnace at a temperature greater than 300° C., greater than 400° C., greater than 500° C. or greater than 600° C. Similarly, in some embodiments, $C_3N_4$ can be prepared by calcining urea in a muffle furnace at these temperatures for more than 2 hours, more than 3 hours, more than 4 hours or more than 6 hours.

$C_3N_4$ can form complexes with transition metal ions. Transition metals are typically elements of groups 4-11 of the periodic table. They display a typical chemistry including formation of a large range of complex ions in various oxidation states and can exhibit catalytic properties either as the element or as ions (or both). Transition metals with catalytic properties that may be useful in various embodiments include, for example, one or more of Ni, Fe, Cu, Pt, Pd, and Co.

Cobalt is one of the abundant metals found in the Earth's crust. In fact, cobalt comprises about 0.0029% of the Earth's crust and, compared to some other transition metals, is relatively inexpensive to use as catalyst. Cobalt exists in many oxidation states ranging from −3 to +5. However, cobalt compounds in the $Co^{2+}$ and $Co^{31}$ states are the most common. Cobalt compounds include cobalt oxides, cobalt sulfides, and cobalt halides. The cobalt oxides includes cobalt(II) oxide or cobalt monoxide (CoO), cobalt(II, III) oxide ($Co_3O_4$), and cobalt(III) oxide ($CO_2O_3$). The cobalt sulfides include cobalt(II) sulfides such as $CoS_2$, and cobalt (III) sulfide ($Co_2S_3$). Four dihalides of cobalt(II) include cobalt(II) fluoride ($CoF_2$), cobalt(II) chloride ($CoCl_2$), cobalt(II) bromide ($CBr_2$), and cobalt(II) iodide ($CoI_2$). The halides exist in both anhydrous and hydrated forms.

Transition metal ions may be capable of forming coordination complexes with $C_3N_4$. In one embodiment, $C_3N_4$ can form a complex with a Pt ion. In another embodiment, $C_3N_4$ can form a complex with a Pd ion. In yet another embodiment, $C_3N_4$ can form a complex with a cobalt ion. The cobalt ion can form a metal-ligand complex with $C_3N_4$ ($Co^{2+}$-carbon nitride complex) in its different oxidation states including, but not limited to, $Co^+$, $Co^{2+}$ and $Co^{3+}$. In one embodiment, $C_3N_4$ forms a complex with $Co^{2+}$ to produce $Co^{2+}$—$C_3N_4$.

$Co^{2+}$—$C_3N_4$ can be formed by loading cobalt on $C_3N_4$. In one embodiment, $C_3N_4$ can be mixed with a cobalt dichloride in a polar solvent to form a mixture or a dispersion. In some embodiments, the mixture/dispersion can also include a base. The mixture can then be subsequently stirred for an hour and heated in a microwave reactor at about 80° C. for about 120 min. In some embodiments, mixing can be achieved by stirring the dispersion comprising $C_3N_4$ into the solution containing cobalt ions. Stirring can be achieved by a repeated manual stirring process or by using a magnetic stirrer. In some embodiments, a dispersant, for example a polymer, can also be added to the dispersion to maintain the dispersion for longer time.

In some embodiments, the polar solvent may be a polar aprotic solvent such as, for example, acetonitrile, acetone, dimethyl sulfoxide (DMSO), or N, N-Dimethylformamide (DMF). However, in some other embodiments, the polar solvent may be a polar protic solvent, and it may include, for example, one or more of water, ammonia, t-butanol, n-propanol, ethanol, methanol, and acetic acid. In one embodiment, the polar solvent is acetonitrile.

In some embodiments, the base can be a Schiff base. The Schiff base can be a symmetric base or an asymmetric base. In some embodiments, the symmetric base may be ethylenediamine, diethylenetriamine or triethylenetetramine. In one embodiment, the base is triethylamine.

In various embodiments, the volume ratio of acetonitrile to triethylamine can vary. In one embodiment, the volume ratio of acetonitrile to triethylamine can be 115.4:1. In other embodiments, the volume ratio of acetonitrile to triethylamine can be 100:1. In another embodiment, the volume ratio of acetonitrile to triethylamine can be 150:1. In yet other embodiments, the volume ratio of acetonitrile to triethylamine can be from 50:1 to 300:1, from 50:1 to 100:1, from 100:1 to 150:1, or from 150:1 to 300:1.

While $C_3N_4$ and cobalt dichloride can react at room temperature to form $Co^{2+}$—$C_3N_4$, the reaction can be accelerated by heating. Heating can be done either by using a traditional heating source, for example, a hot plate/stove or by using a microwave oven. In some embodiments, the temperature of the dispersion being reacted can be between 50° C. and 100° C., between 60° C. and 100° C. or between 70° C. and 90° C. Similarly, duration of the reaction time can also vary. In some embodiments, the dispersion can be heated for more than 30 minutes, more than 60 minutes or more than 120 minutes.

Loading efficiency of cobalt on $Co^{2+}$—$C_3N_4$ depends on many factors including the presence or absence of a promotor in the dispersion. Bases such as triethylamine (TEA) promote coordination of cobalt ions with nitrogen atoms in $C_3N_4$ to form $Co^{2+}$—$C_3N_4$, and therefore higher cobalt loadings on $Co^{2+}$—$C_3N_4$ can be achieved in presence of a base. The base helps (1) $Co^{2+}$ to coordinate cobalt with the available nitrogen atoms ("N atoms") of $C_3N_4$, and (2) helps $Co^{2+}$ deposit on $C_3N_4$ as $CoO_x$ at higher cobalt loadings. However, coordination between $Co^{2+}$ and nitrogen can be achieved even without TEA but it may take longer. In the absence of a base, $CoO_x$ does not form easily on $C_3N_4$, even at higher $Co^{2+}$ concentrations.

In various embodiments, the amount of cobalt in the $Co^{2+}$—$C_3N_4$ product can be in the range of 0 to 0.05, 0.05 to 0.1, 0.1 to 0.15, 0.15 to 0.2, 0.2 to 0.25, 0.25 to 0.3, 0.3 to 0.35, 0.35 to 0.4, 0.4 to 0.45, 0.45 to 0.5, 0.5 to 0.6, 0.6 to 0.7, 0.7 to 0.8, 0.8 to 0.9, 0.9 to 1, 1 to 1.2, 1.2 to 1.4, 1.4 to 1.6, 1.6. to 1.8, and 1.8 to 1.10 µmol/mg of $Co^{2+}$—$C_3N_4$. In some embodiments, the amount of cobalt in $Co^{2+}$—$C_3N_4$ can be less than 10, less than 5, less than 2.5, less than 2, less than 1, less than 0.5, less than 0.25, or less than 0.1 µmol/mg of $Co^{2+}$—$C_3N_4$. In the same and other embodiments, the amount of cobalt in $Co^{2+}$—$C_3N_4$ can be more than 0.1, more than 0.5, more than 1, more than 2, more than 3, more than 4, more than 5, or more than 10 µmol/mg of $Co^{2+}$—$C_3N_4$.

Extended X-ray absorption fine structure (EXAFS) analysis of $Co^{2+}$—$C_3N_4$ samples confirm that each $Co^{2+}$ forms four coordinate bonds with four N atoms at edge sites. At low cobalt loadings (e.g., below approximately 0.01 mmol $Co^{2+}$ per gram $Co^{2+}$—$C_3N_4$), greater than 90% of the cobalt exists as $Co^{2+}$ coordinated with N atoms on the $C_3N_4$. At high cobalt loadings, some cobalt can form $CoO_x$ clusters as at higher cobalt loadings available N atoms for coordination may already be occupied by $Co^{2+}$. In some embodiments, at both low and high cobalt loadings, $Co^{2+}$ can be uniformly distributed. Uniform distribution of $Co^{2+}$ means that the cobalt ions are not concentrated in any specific area of the carbon nitride and are evenly distributed across the material.

The $Co^{n+}$ can be positioned outside the plane formed by the nitrogen atoms. For example, the cobalt ion may be outside the plane of the coordinating nitrogen atoms by a distance of greater than 0.1 Angstrom or greater than 0.2 Angstrom and/or less than 0.5 Angstrom.

In $Co^{2+}$—$C_3N_4$, the molar ratio of $Co^{2+}$ to $CoO_x$ may depend on the amount of cobalt reacted with $C_3N_4$. At low cobalt loading, the molar ratio of $Co^{2+}$ to $CoO_x$ can be high. In contrast, at higher loadings, the molar ratio of $Co^{2+}$ to $CoO_x$ can be lower. In various embodiments, the molar ratio of $Co^{2+}$ to $CoO_x$ may be greater than 1, greater than 10, greater than 100, greater than 1000, greater than 10000. In some embodiments, the molar ratio of $Co^{2+}$ to $CoO_x$ may be less than 1, less than 10, less than 100, less than 1000 or less than 10000.

Figure 2:
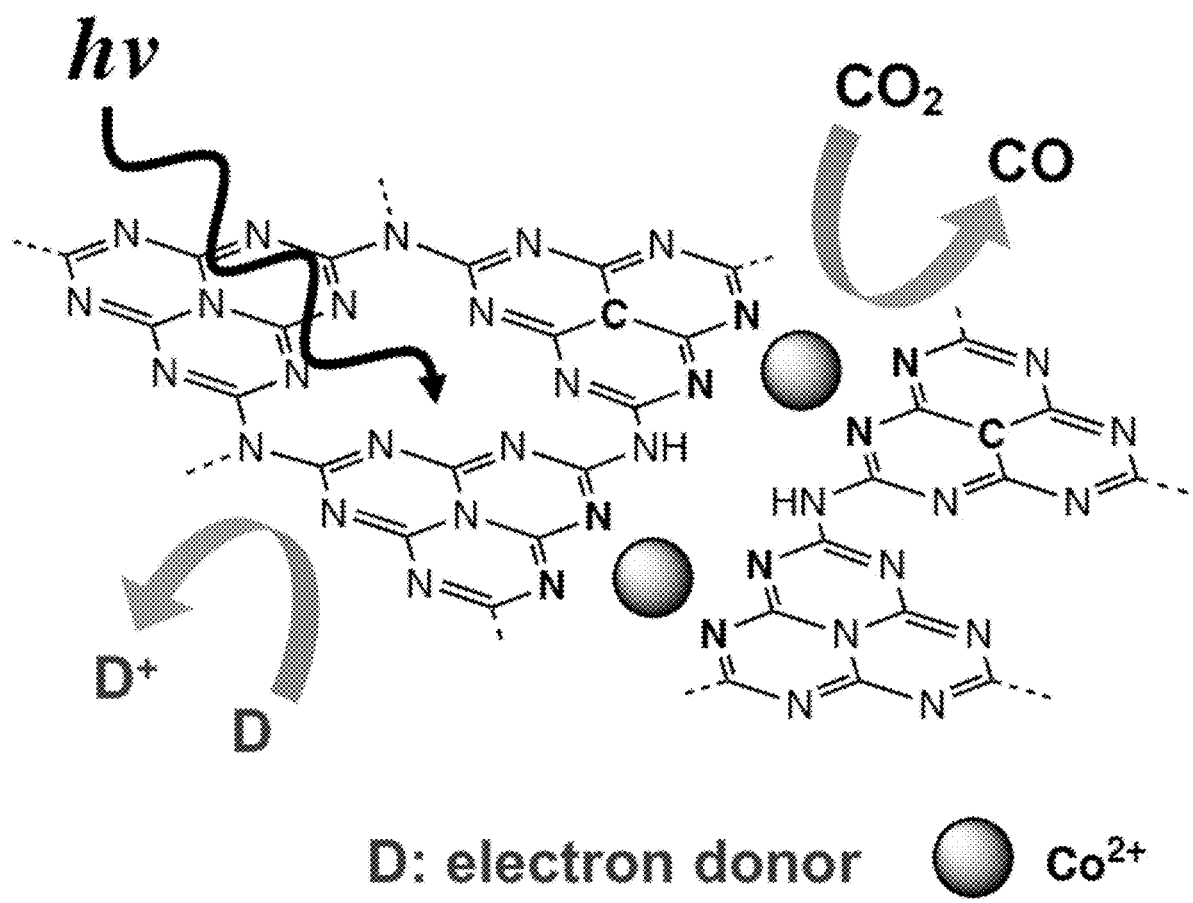
FIG. 2 is a schematic illustration of the photocatalytic reduction of $CO_2$ to CO by single $Co^{2+}$ sites on $C_3N_4$.

$Co^{2+}$—$C_3N_4$ is capable of reducing $CO_2$ to CO under visible light. FIG. 2 is a schematic presentation of the photocatalytic reduction of $CO_2$ to CO mediated by single $Co^{2+}$ sites on $C_3N_4$. $C_3N_4$ can harvest visible light and can activate single $Co^{2+}$ sites without the use of additional ligands and can reduce $CO_2$ to CO selectively. C doping of $C_3N_4$ is considered to be important for the superior $CO_2$-reduction activity using $Co^{2+}$—$C_3N_4$, as discussed in more detail with reference to FIGS. 22-25. In absence of single $Co^{2+}$ sites, $C_3N_4$ has been shown to be unable to catalyze the reduction of $CO_2$ to CO. As used herein, visible light has a wavelength in the range of 400 nm to 800 nm. In some embodiments, the visible light source can irradiate $Co^{2+}$—$C_3N_4$ in a range of wavelengths between 420 and 650 nm. Sources of visible light can be either solar radiation or an artificial source such as lamp, for example, a halogen lamp.

The photocatalytic reduction of $CO_2$ to CO mediated by $Co^{2+}$—$C_3N_4$ is believed to be a multi-electron transfer process, as shown below:

$$CO_2 + 2H^+ + 2e \rightarrow CO + H_2O$$

In the photocatalytic reduction of $CO_2$ to CO, an electron donor such as TEOA can be used to provide electrons and protons needed for the reaction. In this process, TEOA is transformed to oxidized products, while $CO_2$ is reduced to CO. A halogen lamp can be used to provide photons with wavelength greater than 350 nm as the driving force for the reactions to occur.

Depending on the number of electrons $CO_2$ receives during the photocatalytic reduction process, a number of products can be formed, for example, CO or formic acid (if 2 electrons are received); formaldehyde (if 4 electrons are received); methanol (if 6 are electrons received); and methane (if 8 electrons are received). Besides these carbonaceous products, $H_2$ is another competing side product in photocatalysis. In one embodiment where $Co^{2+}$—$C_3N_4$ is used as a photocatalyst in reduction of $CO_2$, CO is the only carbonaceous product that is formed in measurable quantities. CO accounts for at least 75% of the product and $H_2$ is formed as a side product (accounting for less than 25% of total product). Therefore, $Co^{2+}$—$C_3N_4$ can catalyze $CO_2$ reduction to selectively produce CO. As used herein, a product is selectively produced if no other carbonaceous product is formed upon reducing $CO_2$.

To test the photocatalytic $CO_2$ reduction properties of $Co^{2+}$—$C_3N_4$, $Co^{2+}$—$C_3N_4$ can be dispersed in a polar solvent containing an electron donor in a quartz test tube, and $CO_2$ can be bubbled into the dispersion (in the dark) and followed by irradiation with a visible light source. In one embodiment, the photocatalytic reduction of $CO_2$ yields CO as major products. Substantial saturation can be achieved by bubbling $CO_2$ into the dispersion at a rate of about 0.01 standard cubic feet per hour (SCFH), or 5 mL/min or 0.2 mmol/min for a period of 20 minutes. In some embodiments, $CO_2$ can be introduced in its highly pure form (99.999% purity). In other embodiments, $CO_2$ can be introduced in the form of air or a gaseous mixture such as combustion gases.

In some embodiments, the polar solvent may be a polar aprotic or a polar protic solvent, as described above. In one embodiment, the polar solvent is acetonitrile.

In various embodiments, the sacrificial electron donor may include, for example, an aliphatic amine or an aromatic amine or benzyl-dihydronicotinamide (BNAH) or dimethylphenylbenzimidazoline (BIH) or ascorbic acid or an oxalate or a thiol or mixtures thereof. In one embodiment, the sacrificial electron donor is TEOA.

In various embodiments, the volume ratio of polar solvent to electron donor can vary. In one embodiment, the volume ratio of polar solvent to electron donor can be 4:1. In some other embodiments, the volume ratio of polar solvent to electron donor can be 2:1. In another embodiment, the volume ratio of polar solvent to electron donor can be 10:1. In yet other embodiments, the volume ratio of polar solvent to electron donor can be from 2:1 to 10:1, from 1:1 to 8:1, or from 2:1 to 6:1.

$Co^{2+}$—$C_3N_4$ can be reused or recycled many times in the photocatalytic reduction of $CO_2$ to CO process. The photocatalyst, $Co^{2+}$—$C_3N_4$, may be collected from the dispersion after the reduction of $CO_2$. Collection techniques can include, for example, filtration and centrifugation, and the material can be further used with no significant loss of photocatalytic activity after washing with, for instance, acetonitrile.

EXPERIMENTS AND RESULTS

Preparation OF $C_3N_4$ $C_3N_4$ was prepared by pyrolysis of urea (98% purity). Twenty grams of urea was weighed into a covered crucible and was calcined in a muffle furnace at 600° C. for 4 hours (with a ramp rate 5° C./min) to prepare $C_3N_4$. Further experiments indicate that this $C_3N_4$ sample contains doped carbon atoms, e.g., carbon atoms that are not covalently bound in the graphitic structure or that replace some of the N atoms. $Co^{2+}$—$C_3N_4$ without carbon doping has been shown to be incapable of reducing $CO_2$ to CO, as described below.

Preparation of Carbon-Doped Carbon Nitride (C(x)—$C_3N_4$)

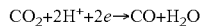

C(x)—$C_3N_4$ samples were also prepared to examine the effect of C doping on the activity of $C_3N_4$ prepared by the pyrolysis of urea. In order to prepare C(x)—$C_3N_4$, different amounts of dextrose and 20 g urea (purity>99.6%) were uniformly mixed and thoroughly ground, and then the mixture was transferred into a covered crucible and calcined in a muffle furnace at 600° C. for 4 h (ramp rate 5° C./min).

Preparation OF $Co^{2+}$—$C_3N_4$

A $Co^{2+}$—$C_3N_4$ sample was formed by coordinating cobalt ions with $C_3N_4$. 100 mg $C_3N_4$ was mixed with a desired amount of $CoCl_2$ in 7.5 mL acetonitrile. The amount of $CoCl_2$ depended on the desired loading of $Co^{2+}$ in the complex. Subsequently, 65 L of TEA was added to the mixture, and then the mixture was stirred for an hour. A capped reaction vessel containing the mixture was placed in a single-mode microwave reactor (CEM Discover), and was heated to 80° C. for 120 min. After 120 min, the resulting precipitate was recovered from the capped reaction vessel by centrifugation and was washed twice with chloroform, methanol and acetonitrile sequentially. The precipitate obtained was dried at room temperature, and the resulting precipitate was denoted as "$Co^{2+}$—$C_3N_4$". Following the same method, $Co^{2+}$—$C_3N_4$ samples were synthesized in the absence of TEA. Single $C^{2+}$ sites were also deposited on C(x)—$C_3N_4$ samples following the same procedure.

A control sample, $CoO_x/SiO_2$ with cobalt loading 0.254 µmol/mg and denoted as "$CoO_x/SiO_2$," was synthesized using 100 mg $SiO_2$ and 5.0 mg $CoCl_2$ in the presence of TEA.

A standard cobalt complex, Co-cyclam, a molecular catalyst, was synthesized using a method as described here. Cobalt(II) chloride (1.3 g) dissolved in 30 mL methanol was added to a solution of the 1,4,8,11-tetraazacyclotetradecane (cyclam) (2.0 g) in 20 mL methanol to form a brown-colored solution, and then air was bubbled through the brown solution for 1 hr. One hour later, concentrated hydrochloric acid (3 ml) was added which resulted in a change in color of the solution from brown to deep green. Air was bubbled through the solution for an additional hour, and then the solution was filtered and evaporated to dryness. The green residue was recrystallized using a minimum volume of water at 80° C., and the green needle crystals formed were filtered off and washed with acetone and ether sequentially.

Preparation of Low-$Co^{2+}$—$C_3N_4$ and High-$Co^{2+}$—$C_3N_4$ Complexes

In $Co^{2+}$—$C_3N_4$, the cobalt loading can be varied by reacting different amounts of $CoCl_2$. In presence of TEA, the cobalt concentration in $Co^{2+}$—$C_3N_4$ was varied between 0.004 and 0.430 µmol of $Co^{2+}$ per mg of $Co^{2+}$—$C_3N_4$. However, when the reaction was carried out in the absence of TEA, the highest cobalt loading successfully achieved was only 0.016 µmol/mg even when an excess of $CoCl_2$ was used in the reaction. A $Co^{2+}$—$C_3N_4$ complex loaded with 0.016 µmol of $Co^{2+}$ per mg of $Co^{2+}$—$C_3N_4$ is referred to herein as "low-$Co^{2+}$—$C_3N_4$," whereas a $Co^{2+}$—$C_3N_4$ loaded with 0.430 µmol of $Co^{2+}$ per mg of $Co^{2+}$—$C_3N_4$ is referred to herein as "high-$Co^{2+}$—$C_3N_4$."

Figure 3:
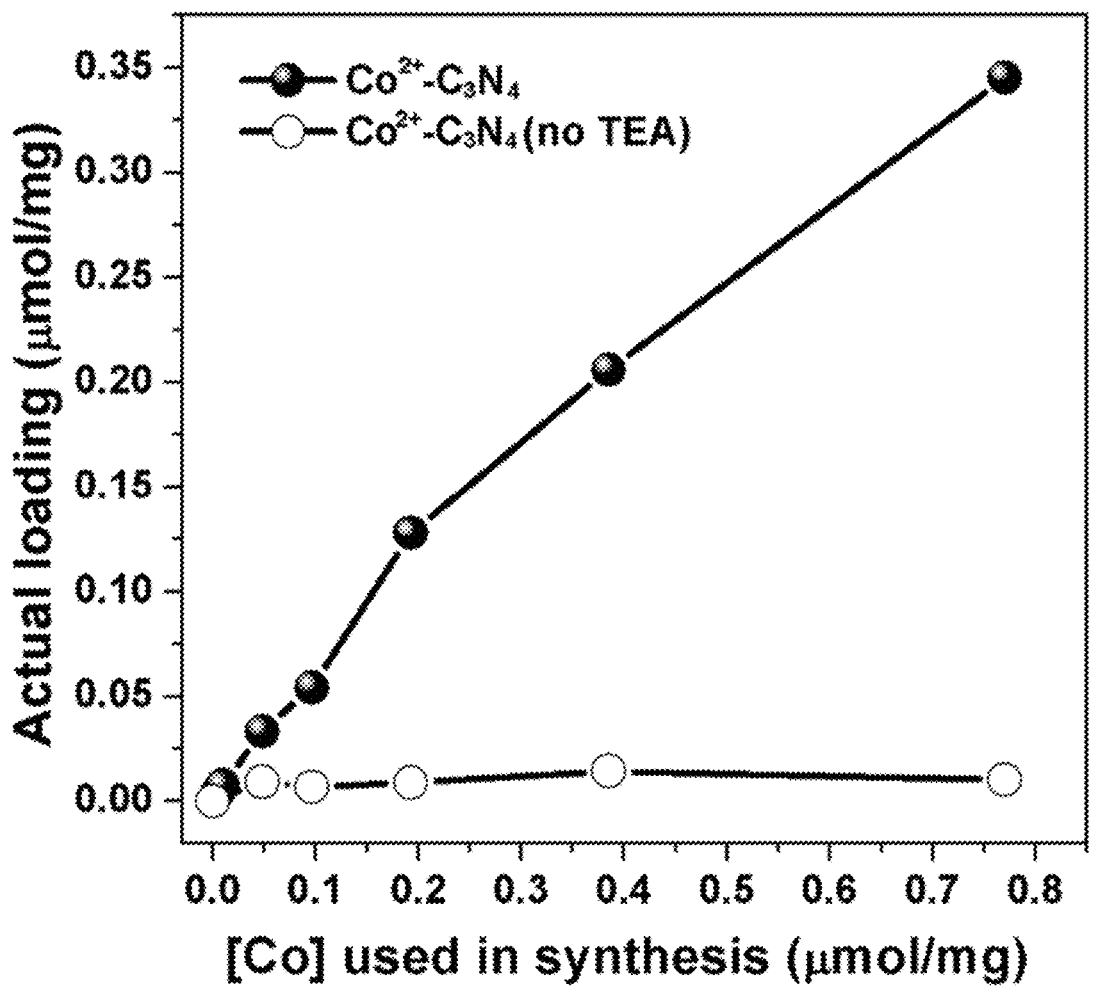
FIG. 3 illustrates amounts of cobalt loadings on $Co^{2+}$—$C_3N_4$ prepared in presence (solid cycle) and absence (open cycle) of triethylamine (TEA) using different amounts of $CoCl_2$ in the synthesis.

FIG. 3 shows the actual cobalt loadings in $Co^{2+}$—$C_3N_4$ prepared in the presence and absence of TEA at different amounts of $CoCl_2$ used in the synthesis. In the reaction mixture of TEA, as the amount of $CoCl_2$ in the reaction mixture increases, the concentration of cobalt in $Co^{2+}$—$C_3N_4$ also linearly increases. In fact, approximately 45% of $CoCl_2$ used in reaction mixture in the presence of TEA was successfully loaded on $C_3N_4$. However, in the absence of TEA, the concentration of cobalt in $Co^{2+}$—$C_3N_4$ does not increase in proportion to the increase in the amount of $CoCl_2$.

Material Characterization

Elemental analysis was conducted by acid digestion, followed by quantification using a Varian Vista AX induced coupled plasma atomic emission spectrometer. X-ray diffraction (XRD) patterns of powder samples were collected on a Rigaku XDS 2000 diffractometer using nickel-filtered Cu Kα radiation (λ=1.5418 Å). Scanning electron microscopy (SEM) images and energy dispersive spectroscopy (EDS) were collected on an Amray 3300FE field emission SEM with PGT Imix-PC microanalysis system. Transmission electron microscopy (TEM) images were obtained on a Zeiss/LEO 922 Omega system. X-ray photoelectron spectra (XPS) were collected on a Kratos Axis HS XPS system. UV-visible spectra were obtained on a Cary 50 Bio spectrophotometer. A Barrelino diffuse reflectance probe was used to collect UV-visible spectra of powder samples using BaSO4 as a standard. Transmission FTIR spectra were collected on a Thermo Nicolet iS10 FTIR spectrometer. Results are shown in FIGS. 4, 5A-B, 7, 8A-F, and 9, and are described below.

Figure 4:
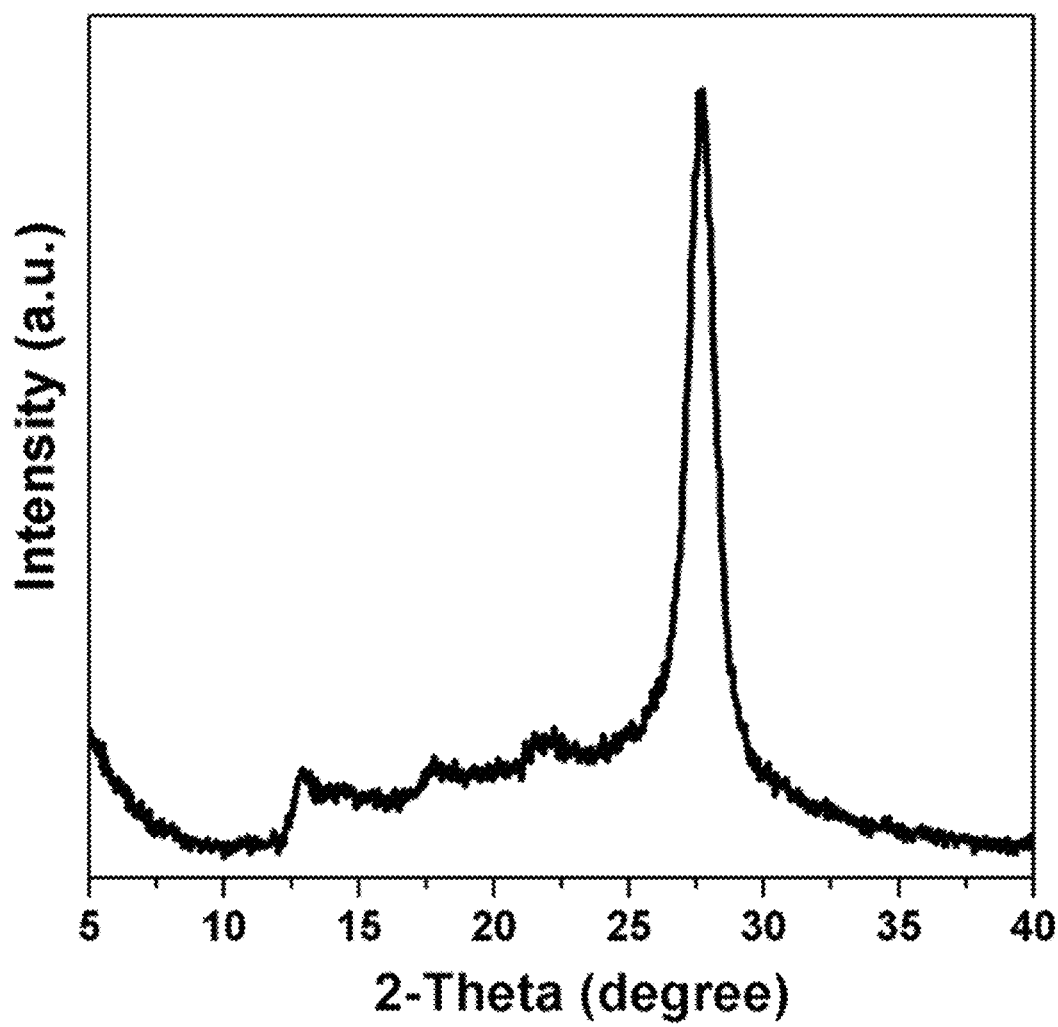
FIG. 4 illustrates X-ray powder diffraction (XRD) pattern of bare $C_3N_4$. Bare $C_3N_4$ denotes $C_3N_4$ without any cobalt or other kinds of loadings.

FIG. 4 shows XRD pattern of $C_3N_4$ prepared by pyrolysis of urea as described above.

Figure 5A:
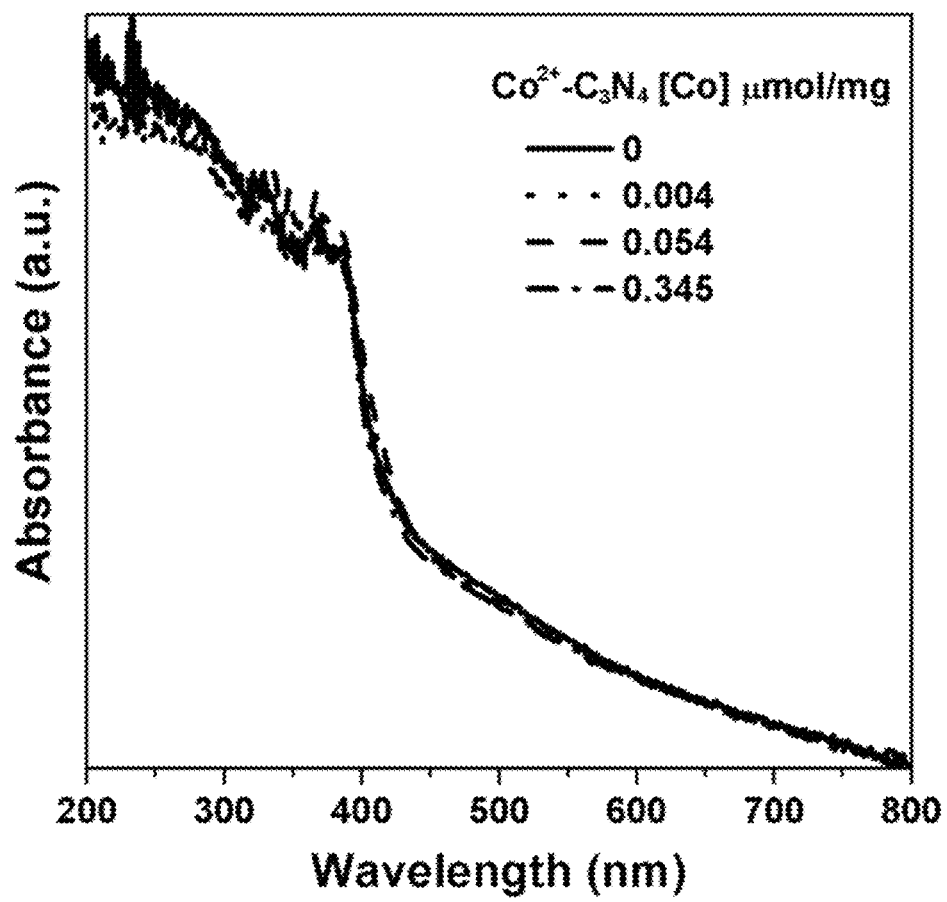
FIG. 5A illustrates optical spectra of bare $C_3N_4$ and $Co^{2+}$—$C_3N_4$ with different amounts of cobalt loadings.
Figure 5B:
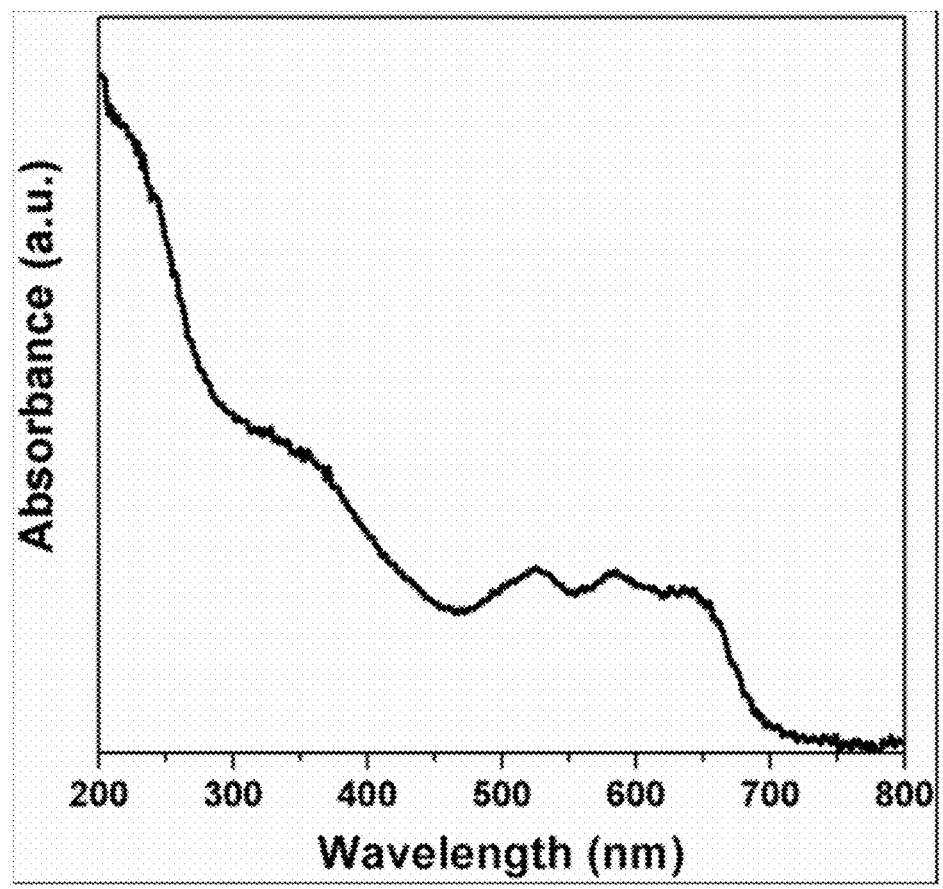
FIG. 5B illustrates an optical spectrum of $CoO_x/SiO_2$ in the powder form. The peaks between 500 nm and 700 nm are associated with cobalt oxides.
Figure 6:
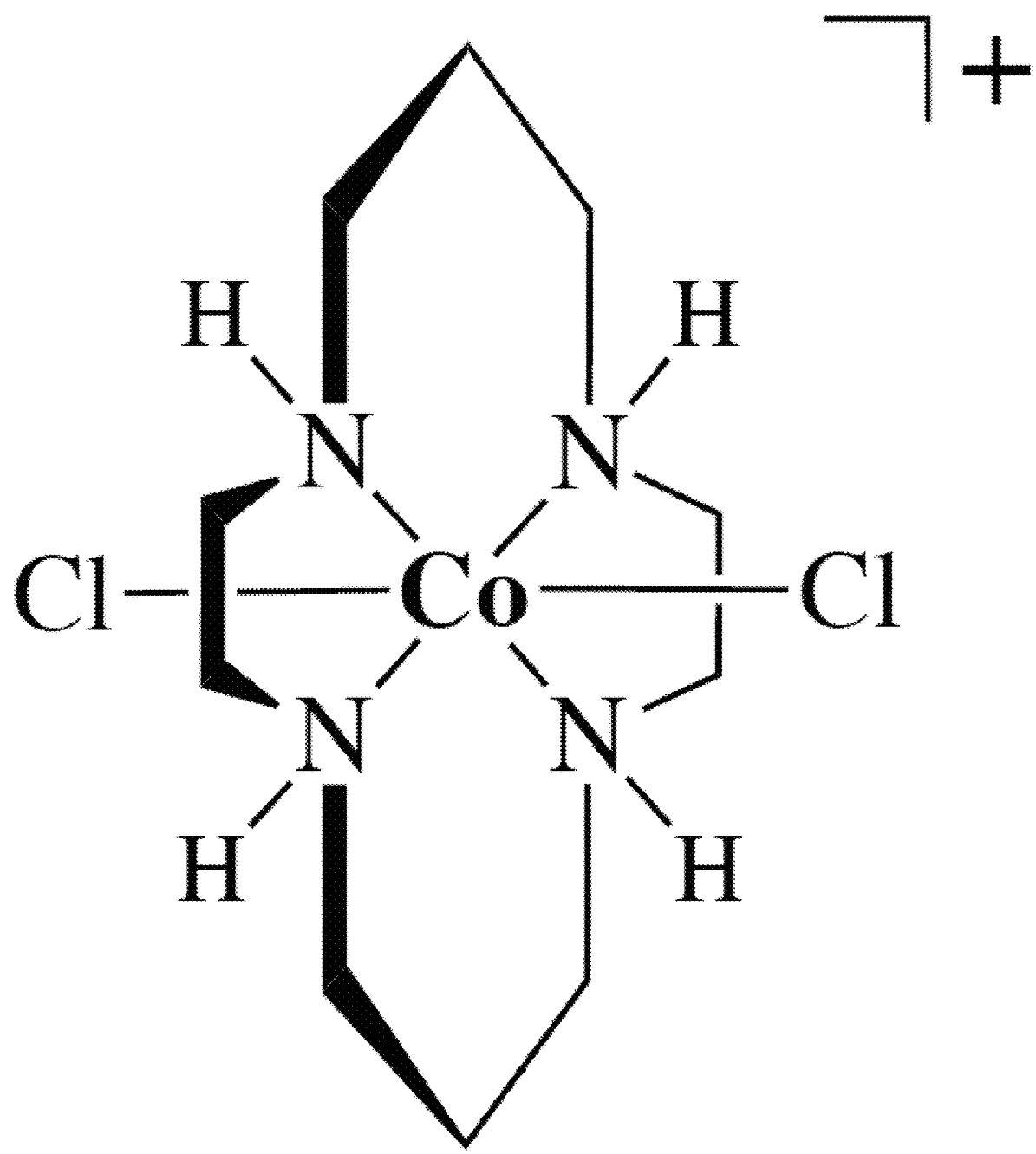
FIG. 6 illustrates the structure of Co-cyclam, a molecular catalyst that contains a macrocyclic ligand (cyclam).

FIG. 5A shows the optical spectra of $C_3N_4$ with 0, 0.004, 0.054, and 0.345 µmol of $Co^{n+}$ loadings per mg of $Co^{2+}$—$C_3N_4$. The optical spectrum of bare $C_3N_4$ prepared from 98% urea, that is, $Co^{2+}$—$C_3N_4$ with no $Co^{2+}$ or any other loading, exhibits significant photoresponse in the visible region (400-800 nm). Loading of $Co^{2+}$ on $C_3N_4$ does not result in any notable change in the optical spectrum of $C_3N_4$. FIG. 5B shows the optical spectra of $CoO_x/SiO_2$, a control sample. The peaks between 500 and 700 nm are associated with cobalt oxides.

Figure 7:
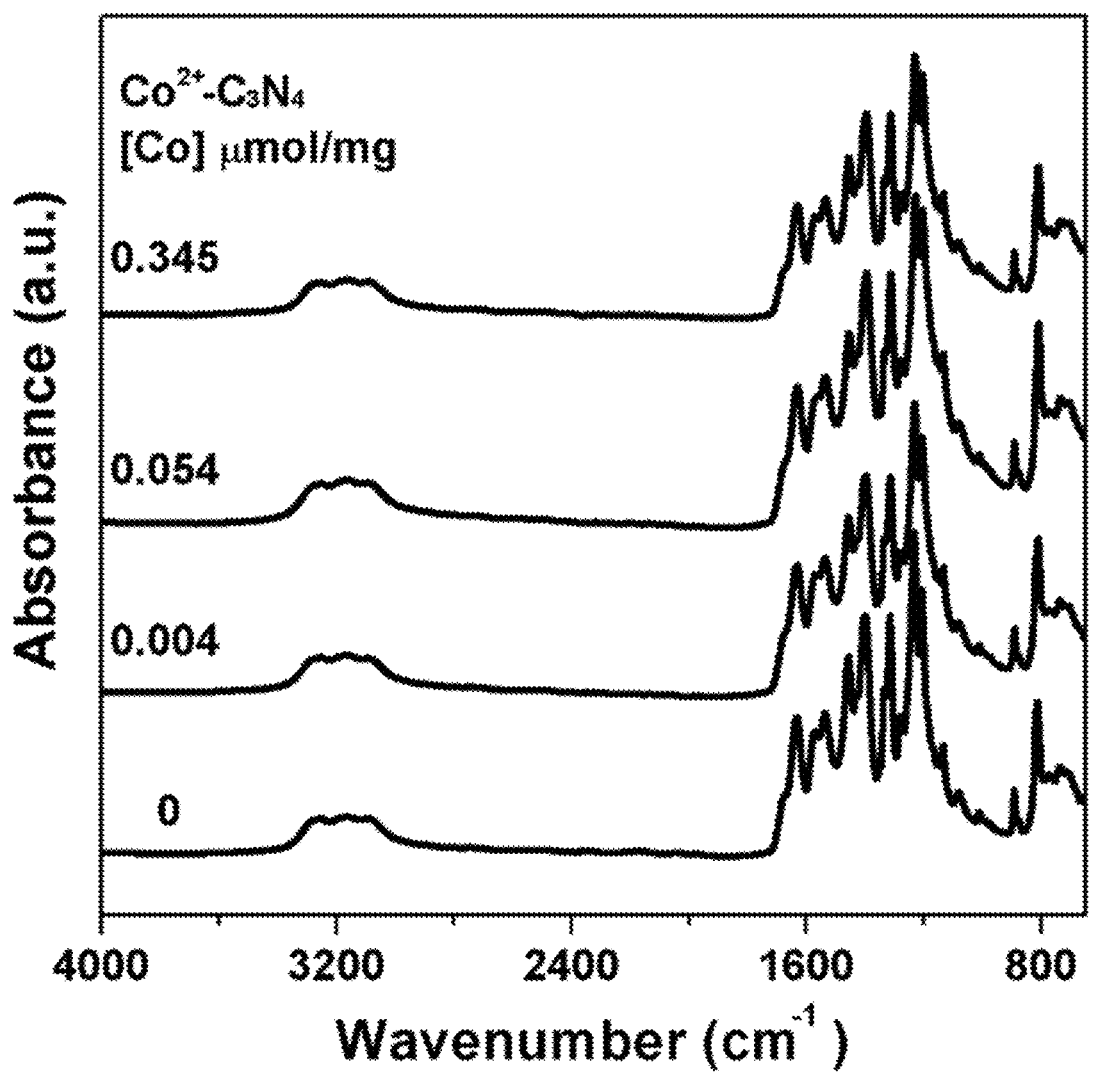
FIG. 7 illustrates infrared spectra of bare $C_3N_4$ and $Co^{2+}$—$C_3N_4$ with different amounts of cobalt loadings.

FIG. 7 shows the infrared spectra of $C_3N_4$ with 0, 0.004, 0.054, and 0.345 µmol of $Co^{2+}$ loadings per mg of $Co^{2+}$—$C_3N_4$. The infrared spectra of $Co^{2+}$—$C_3N_4$ samples are almost identical to that of bare $C_3N_4$, confirming that the cobalt loading does not affect the structure of $C_3N_4$.

FIGS. 8A-D show TEM and SEM images of bare $C_3N_4$ and $Co^{2+}$—$C_3N_4$. There is no discernible difference in the morphologies of bare $C_3N_4$ and $Co^{2+}$—$C_3N_4$ as seen in their TEM and SEM images. That indicates that $Co^{2+}$ on $C_3N_4$ does not result in any measurable morphological changes to the $C_3N_4$. This confirms that the process, as described above, used for loading cobalt on $C_3N_4$ does not affect $C_3N_4$ morphology.

Figure 8:
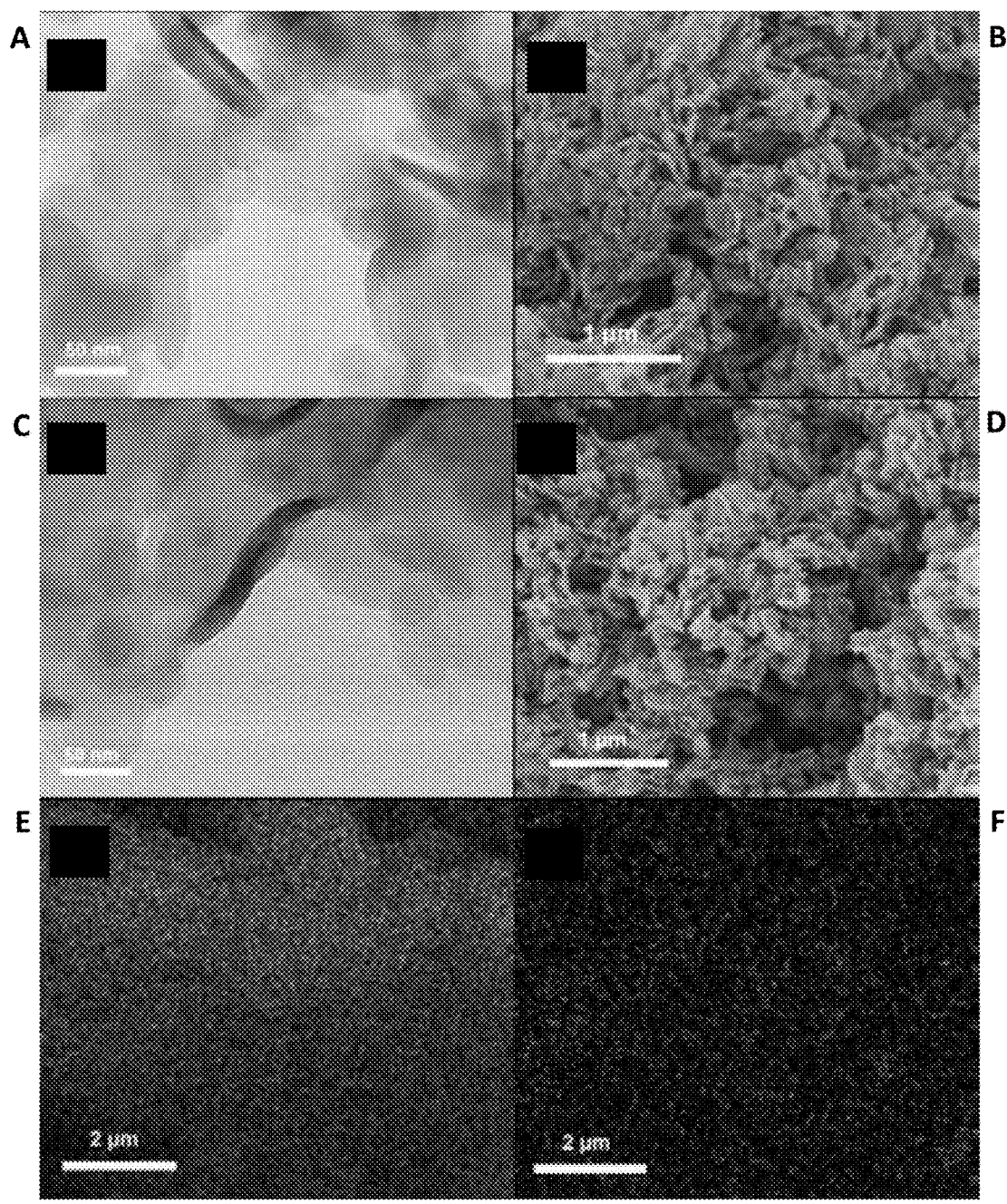
FIG. 8A-F illustrate (A) TEM and (B) SEM images of bare $C_3N_4$; (C) TEM image, (D) SEM image of $Co^{2+}$—$C_3N_4$ with a cobalt loading of 0.345 μmol/mg; and elemental distribution of (E) nitrogen atoms and (F) Co of $Co^{2+}$—$C_3N_4$ with a cobalt loading of 0.345 μmol/mg.

FIGS. 8E and 3F show elemental distribution of nitrogen atoms and cobalt atoms, respectively, in a $Co^{2+}$—$C_3N_4$ sample with a cobalt loading of 0.345 µmol/mg of $Co^{2+}$—$C_3N_4$. The microscopic mapping of $Co^{2+}$—$C_3N_4$ reveals that $Co^{2+}$ is uniformly distributed on $C_3N_4$ within $Co^{2+}$—$C_3N_4$ structure.

Figure 9:
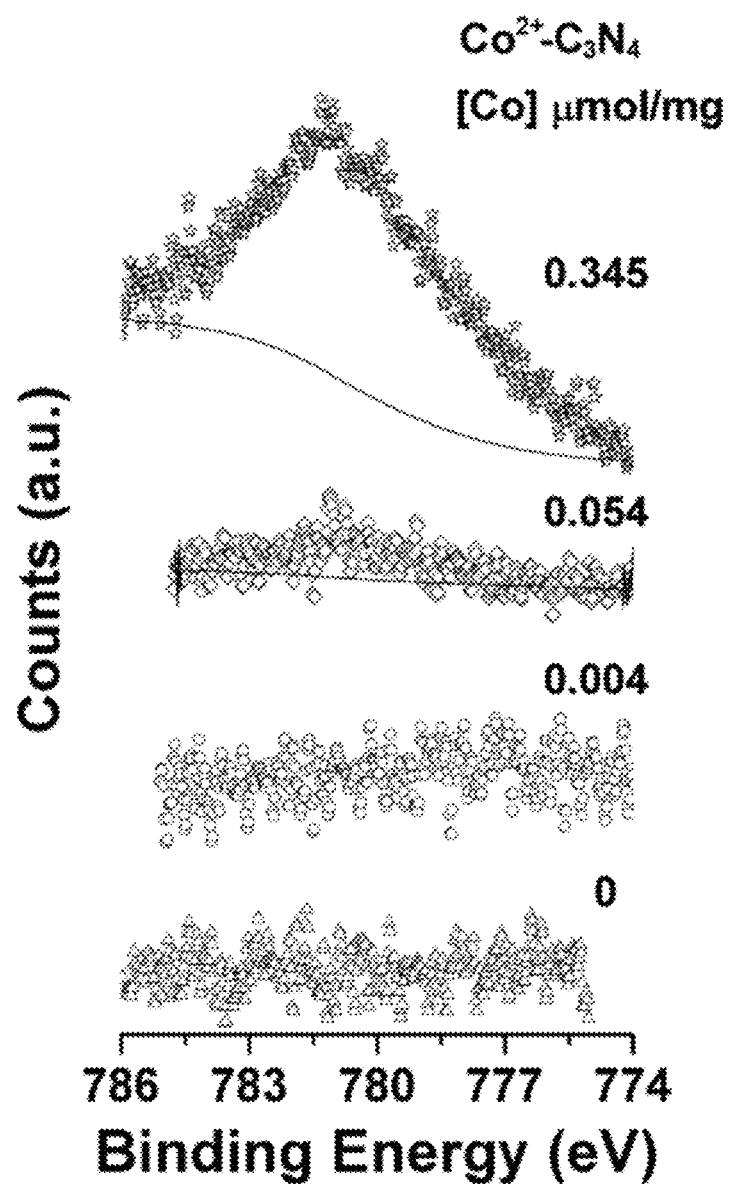
FIG. 9 illustrates X-ray photoelectron spectra (XPS) of bare $C_3N_4$ and $Co^{2+}$—$C_3N_4$ with different amounts of cobalt loadings.

FIG. 9 shows XPS spectra of four $Co^{2+}$—$C_3N_4$ samples with 0, 0.004, 0.054, and 0.345 µmol of $Co^{2+}$ loadings per mg of $Co^{2+}$—$C_3N_4$. The presence of a peak at 781 eV in the spectra of cobalt loaded samples confirms the presence of $Co^{2+}$ sites in $Co^{2+}$—$C_3N_4$. However, when the cobalt loading is zero (i.e. in the bare $C_3N_4$ sample), the cobalt peak is absent. This confirms that the $Co^{2+}$—$C_3N_4$ includes $Co^{2+}$ sites.

Figure 13:
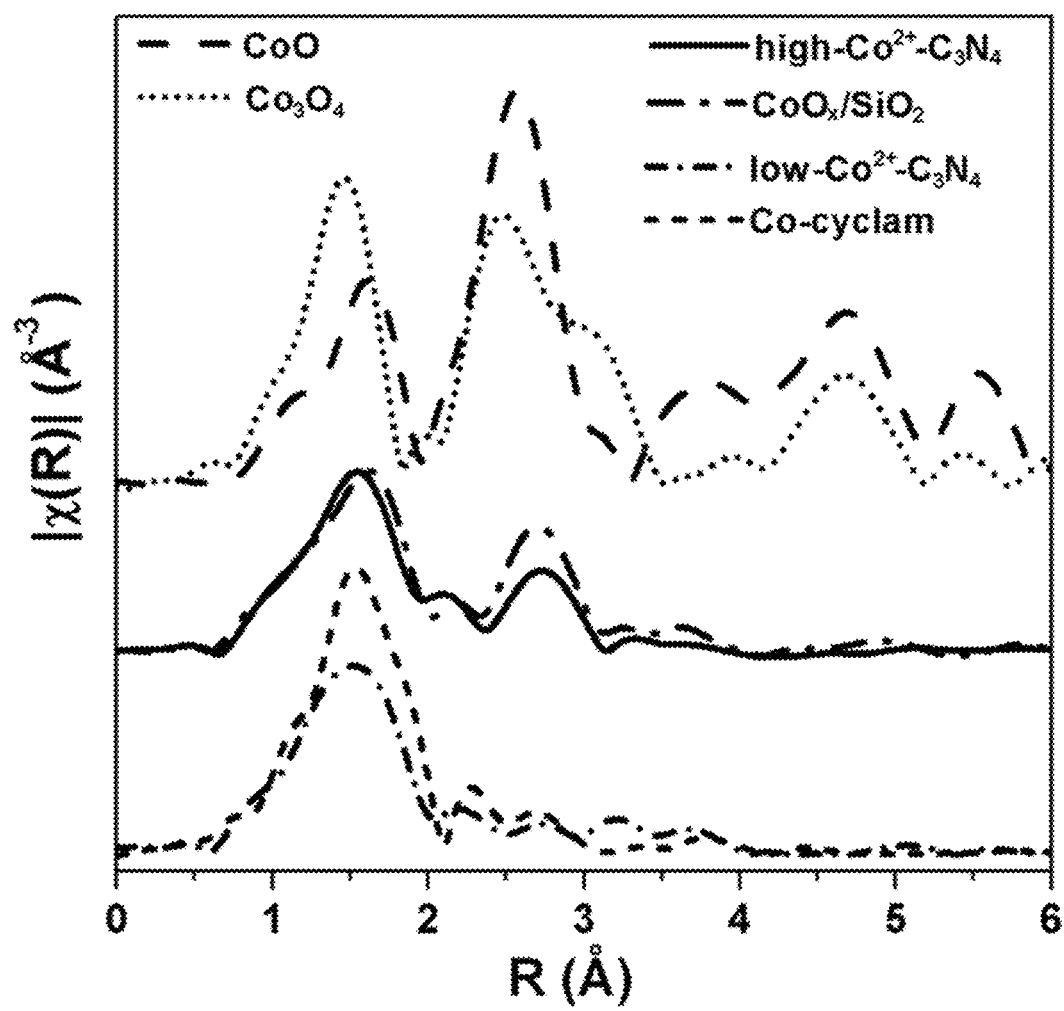
FIG. 13 illustrates a Fourier transform magnitude of $k^2$-weighted Co K-edge extended X-ray absorption fine structure (EXAFS) spectra of Co-cyclam, high-$Co^{2+}$—$C_3N_4$, low-$Co^{2+}$—$C_3N_4$, $CoO_x/SiO_2$, CoO, and $Co_3O_4$.

X-ray absorption spectra at Co K-edge were taken at the beamline 7-BM (QAS) of NSLS-II at Brookhaven National Laboratory. Si (111) double crystal was used as monochromator and detuned 30% to reduce harmonics. The 15-cm long ion chambers, which were filled with 100% $N_2$, were used for detection of incident and transmitted beams, and a passivated implanted planar silicon (PIPS) detector was used for detection of fluorescence from the sample. The beam size was 1.4 mm (vertical)×6 mm (horizontal). Co-cyclam, high-$Co^{2+}$—$C_3N_4$ and $CoO_x/SiO_2$ samples were measured in transmission mode, and the low-$Co^{2+}$—$C_3N_4$ was measured in fluorescence mode. $CoO_x/SiO_2$ was deposited on tape and the other samples were made into 13 mm diameter pellets. At least three scans were measured for each sample. All measurements were performed in ambient atmosphere at room temperature and the samples were held in 45 geometry. A Co foil was placed between the two detectors downstream from the sample and measured simultaneously with the sample as reference for energy alignment. The existing data for Co oxides were aligned with the samples' spectra using their respective reference foil spectra. Results are shown in FIGS. 10, 11, and 13 are described below.

Figure 10:
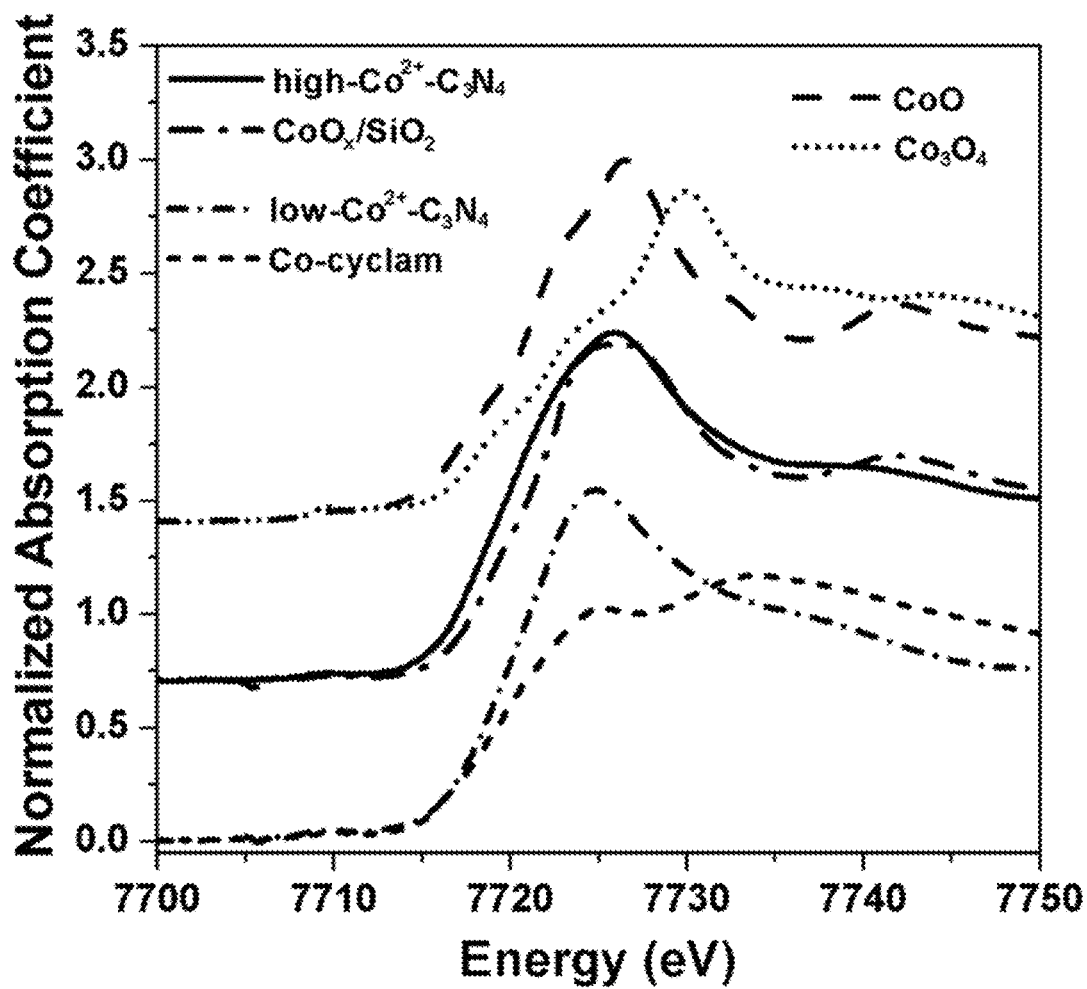
FIG. 10 illustrates normalized Co K-edge X-ray absorption near edge structure (XANES) spectra of Co-cyclam, high-$Co^{2+}$—$C_3N_4$, low-$Co^{2+}$—$C_3N_4$, $CoO_x/SiO_2$, CoO, and $Co_3O_4$.
Figure 11:
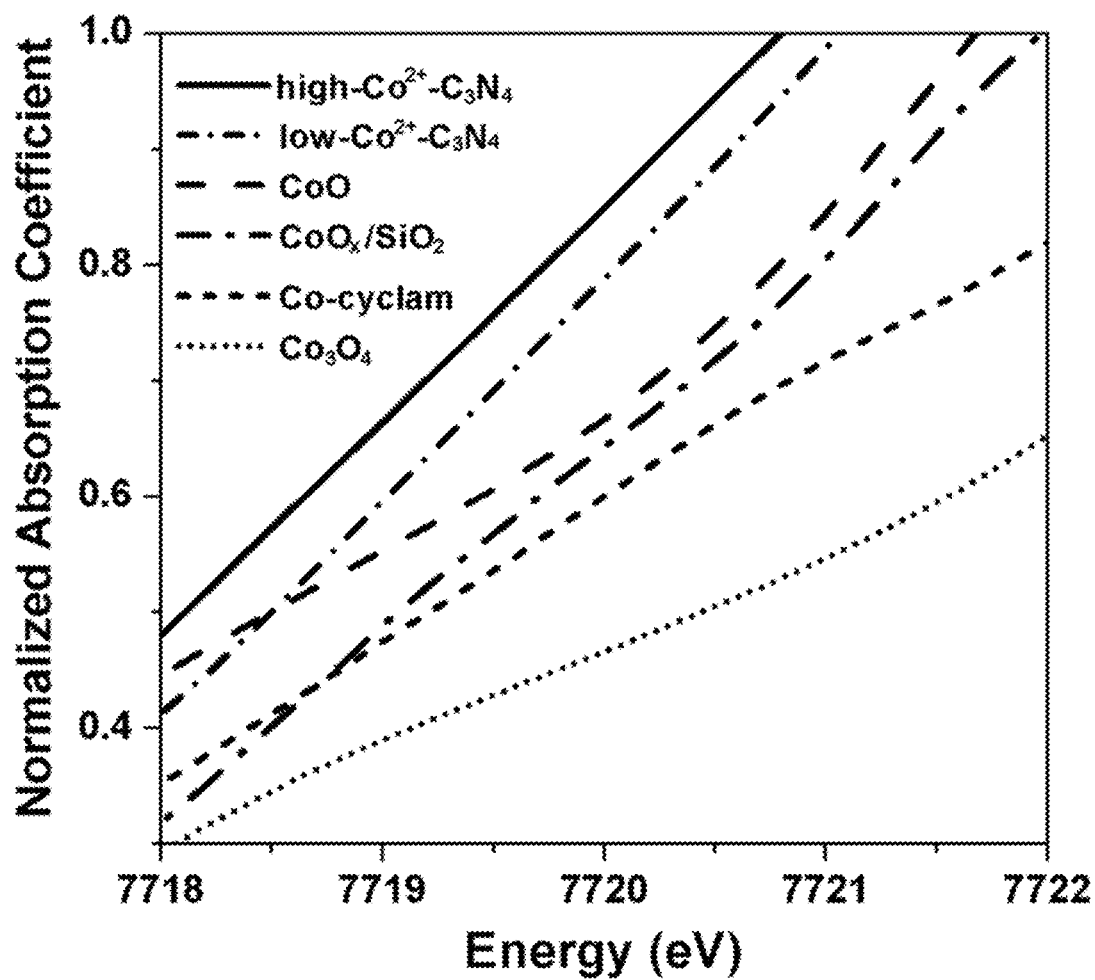
FIG. 11 illustrates a close comparison of normalized Co K-edge XANES spectra of Co-cyclam, high-$Co^{2+}$—$C_3N_4$, low-$Co^{2+}$—$C_3N_4$, $CoO_x/SiO_2$, CoO, and $Co_3O_4$.

FIG. 10 shows normalized Co K-edge XANES spectra of low-$Co^{2+}$—$C_3N_4$ and high-$Co^{2+}$—$C_3N_4$. FIG. 10 also shows Co K-edge XANES spectra of some other cobalt control samples including CoO, $Co_3O_4$, $CoO_x/SiO_2$, and Co-cyclam. FIG. 11 shows a close comparison of normalized Co K-edge XANES spectra shown in FIG. 10. A close comparison of Co K-edge XANES spectra of low-$Co^{2+}$—$C_3N_4$ and high-$Co^{2+}$—$C_3N_4$ with that of other cobalt samples reveals that cobalt is in oxidation state +2 in both low-$Co^{2+}$—$C_3N_4$ and high-$Co^{2+}$—$C_3N_4$ samples, and the oxidation state of cobalt in $Co^{2+}$—$C_3N_4$ is +2. The XANES spectra also indicate that the cobalt species in $CoO_x/SiO_2$ and Co-cyclam are at higher oxidation states than the cobalt in low-$Co^{2+}$—$C_3N_4$ and high-$Co^{2+}$—$C_3N_4$.

FIG. 10 further reveals that $Co^{2+}$ in $Co^{2+}$—$C_3N_4$ is not in the same plane as the plane defined by the flat framework of nitrogen atoms in $C_3N_4$. The flat framework of nitrogen atoms implies that nitrogen atoms in $C_3N_4$ occupy a single plane. The results further indicate that the $Co^{2+}$ ions are off the plane of nitrogen atoms by a distance less than 0.5 Angstrom. This is confirmed by the absence of a shoulder feature along the rising edge around 7715 eV of the normalized Co K-edge XANES spectra of $Co^{2+}$—$C_3N_4$. Co K-edge XANES spectra of Co-porphyrins, a cobalt complex having four-coordinate square-planar structure, typically shows a shoulder feature along the rising edge around 7715 eV. Therefore, it is clear that $Co^{2+}$ in $Co^{2+}$—$C_3N_4$ is not in the same plane formed by the atoms making up the ligand. This is in contrast to the cobalt in a Co-porphyrin where the cobalt and porphyrins share a common plane.

FIG. 10 shows that the shape of Co K-edge XANES spectra of low-$Co^{2+}$—$C_3N_4$ is different from those of CoO and $Co_3O_4$, and this is likely due to the coordination of $Co^{2+}$ with nitrogen atoms of $C_3N_4$ in low-$Co^{2+}$—$C_3N_4$. In contrast, the spectral shapes of high-$Co^{2+}$—$C_3N_4$ and $CoO_x/SiO_2$ are similar to that of the CoO, indicating the presence of CoO in both high-$Co^{2+}$—$C_3N_4$ and $CoO_x/SiO_2$.

Figure 12:
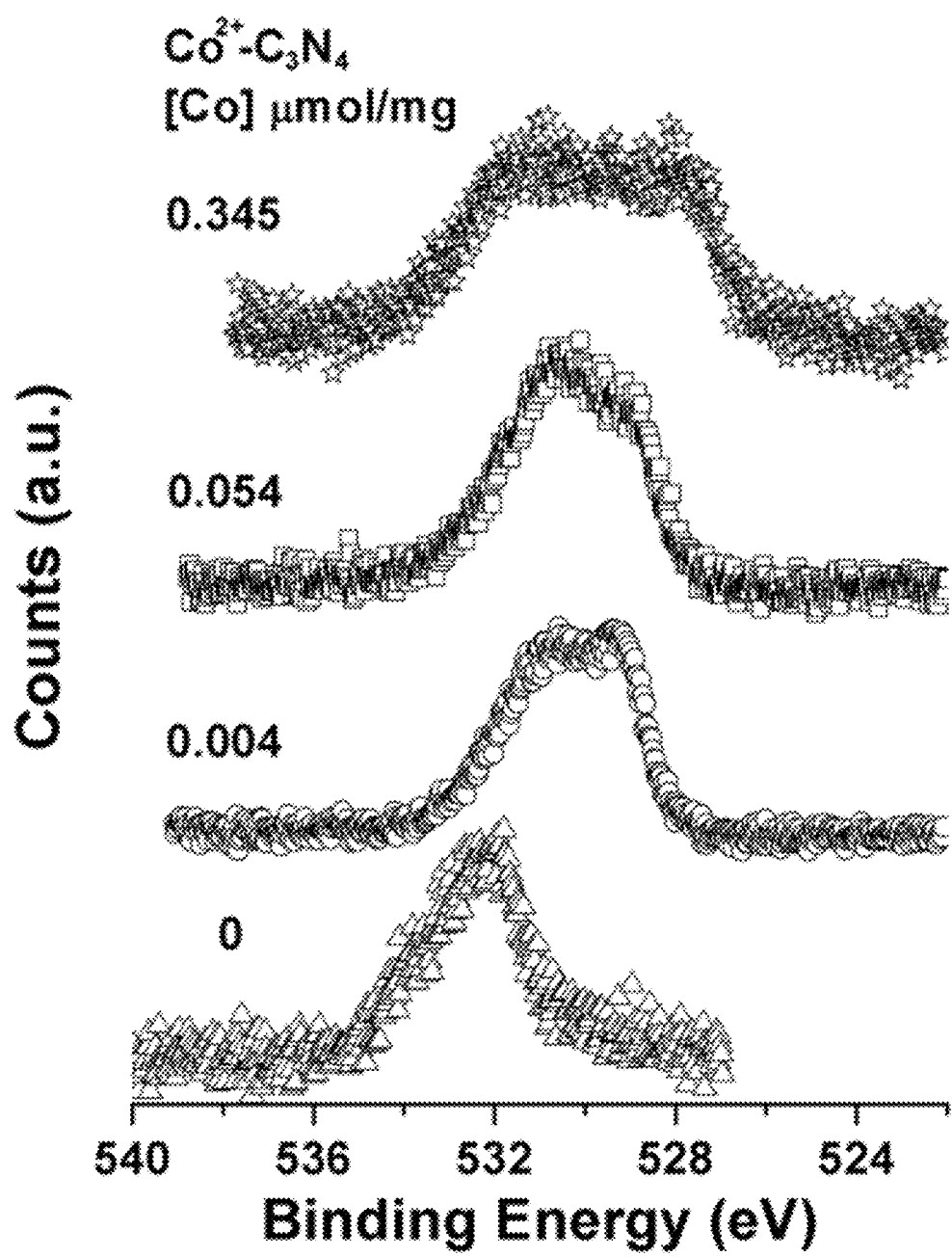
FIG. 12 illustrates O 1s XPS of bare $C_3N_4$ and $Co^{2+}$—$C_3N_4$ with different amounts of cobalt loadings.

FIG. 12 shows the oxygen 1s XPS of bare $C_3N_4$ and $Co^{2+}$—$C_3N_4$ with 0, 0.004, 0.054, and 0.345 μmol of $Co^{2+}$ loadings per mg of $Co^{2+}$—$C_3N_4$. In the spectra of $Co^{2+}$—$C_3N_4$ samples, O 1s peaks that are associated with $O^{2-}$ are seen between 528 eV and 530 eV. This is likely due to the presence of $OH^-$ bound to $Co^{2+}$ as well as CoO in the sample with a cobalt loading of 0.345 μmol of $Co^{2+}$ loadings per mg of $Co^{2+}$—$C_3N_4$. The O 1s XPS spectra also confirms that the presence of CoO in high-$Co^{2+}$—$C_3N_4$.

FIG. 13 shows Fourier transform magnitude of $k^2$-weighted Co K-edge EXAFS spectra of low-$Co^{2+}$—$C_3N_4$, high-$Co^{2+}$—$C_3N_4$, CoO, $Co_3O_4$, $CoO_x/SiO_2$, and Co-cyclam. The spectra of both high-$Co^{2+}$—$C_3N_4$ and low-$Co^{2+}$—$C_3N_4$ exhibit a peak around 1.55 Å (uncorrected for the photoelectron phase shift), which is similar to that of Co-cyclam. This further indicates the coordination of $Co^{2+}$ with nitrogen atoms of $C_3N_4$ in $Co^{2+}$—$C_3N_4$ complexes.

FIG. 13 demonstrates that there is no Co—O—Co (i.e. cobalt-oxygen-cobalt) contribution in low-$Co^{2+}$—$C_3N_4$, indicating that $Co^{2+}$ exists as isolated but is coordinated with four nitrogen atoms of $C_3N_4$. In low-$Co^{2+}$—$C_3N_4$, the cobalt may be unassociated with oxygen atoms, halide atoms or any atoms other than those that comprise the carbon nitride. In contrast, there is a Co—O—Co contribution in high-$Co^{2+}$—$C_3N_4$ indicating that high-$Co^{2+}$—$C_3N_4$ sample contains some cobalt oxides which do not contribute in $CO_2$ reduction to CO, as described later. This confirms that cobalt in low-$Co^{2+}$—$C_3N_4$ exists as isolated single sites. This result highlights the importance of X-ray absorption spectroscopy in establishing that the metal ions in the photocatalyst are atomically dispersed.

Figure 14:
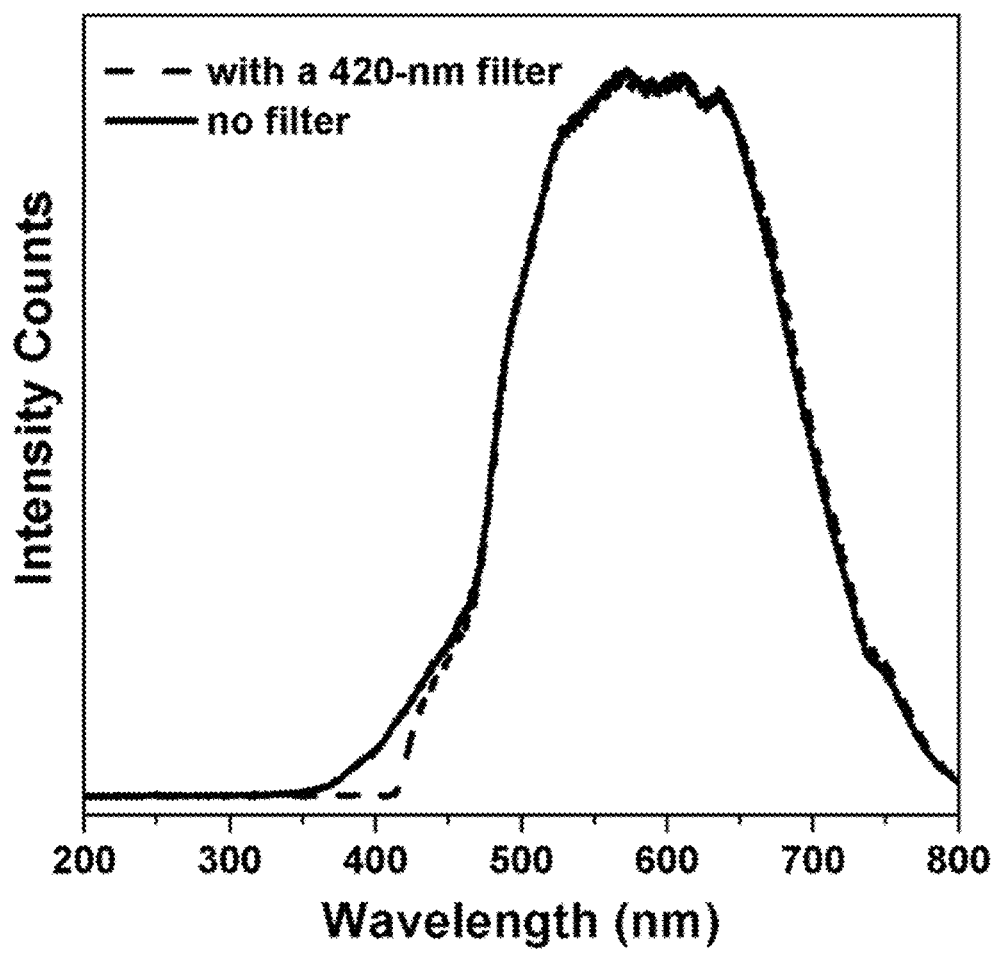
FIG. 14 illustrates output spectra of the halogen lamp, used in this study, with and without a 420-nm long-pass optical filter.

Photocatalytic Reduction of $Co_2$ Under Visible Light $Co^{2+}$—$C_3N_4$ catalyzes the reduction of carbon dioxide under visible light to carbon monoxide. In order to test the photocatalytic $CO_2$ reduction properties of $Co^{2+}$—$C_3N_4$, 1 mg of $Co^{2+}$—$C_3N_4$, was dispersed in a 4.0 mL acetonitrile solution containing triethanolamine (TEOA) (acetonitrile: TEOA=4:1 v/v) in a quartz test tube. Prior to photocatalytic testing, the reaction solution was bubbled with $CO_2$ (99.999%, Airgas) at 5 mL/min in the dark for 20 min. The reaction solution was then irradiated with a halogen lamp equipped with a water filter. FIG. 14 shows the output spectra of the halogen lamp used in this study with (shown in dotted trace) and without (shown in solid trace) a 420-nm long-pass optical filter. In some tests, a long-pass (λ>420 nm) optical filter was used with the lamp. Light intensity on the reaction solution was fixed at 200 mW/cm². The head space above the reaction solution was sampled with a gas-tight syringe at different time intervals for product analysis using an Agilent 7820 gas chromatograph equipped with a thermal conductivity (TCD) detector and a 60/80 Carboxen-1000 packed column (Supelco). In isotope experiments, $^{13}CO_2$ (Sigma-Aldrich, carbon-13 99%) was introduced into a reaction solution containing 4 mg $Co^{2+}$—$C_3N_4$ after degassing the solution through freeze-pump-thaw cycling. The head space above the reaction solution was sampled and analyzed in a gas cell with the Thermo Nicolet iS10 FTIR spectrometer. Results are shown in FIGS. 15A-B and 16, and are described below.

Figure 15:
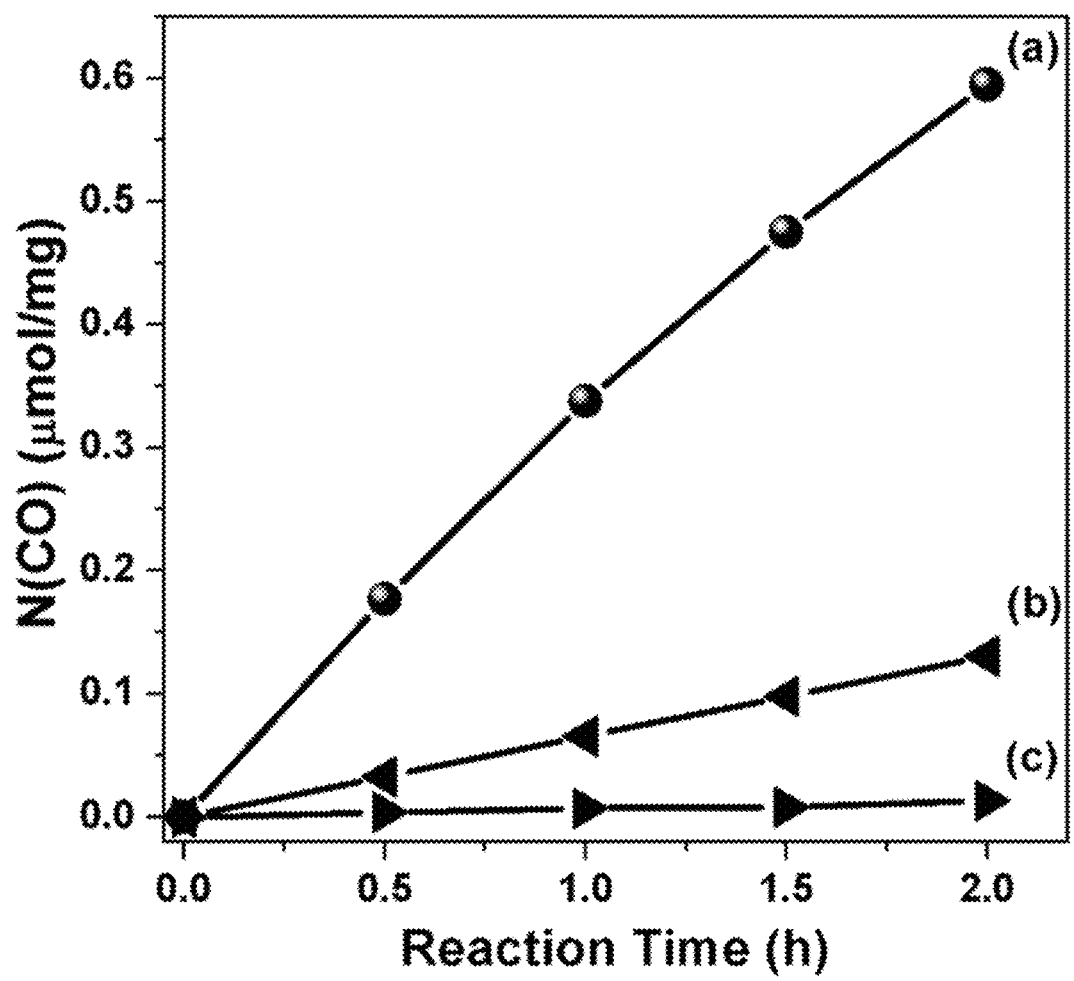
FIG. 15 illustrates the amounts of CO produced in $CO_2$ reduction using (a) 1 mg $Co^{2+}$—$C_3N_4$ with a cobalt loading of 0.054 μmol/mg; (b) a dispersion of 0.054 μmol $CoCl_2$ and 1 mg $C_3N_4$; and (c) 1 mg bare $C_3N_4$ (light intensity 200 mW/cm$^2$).
Figure 16:
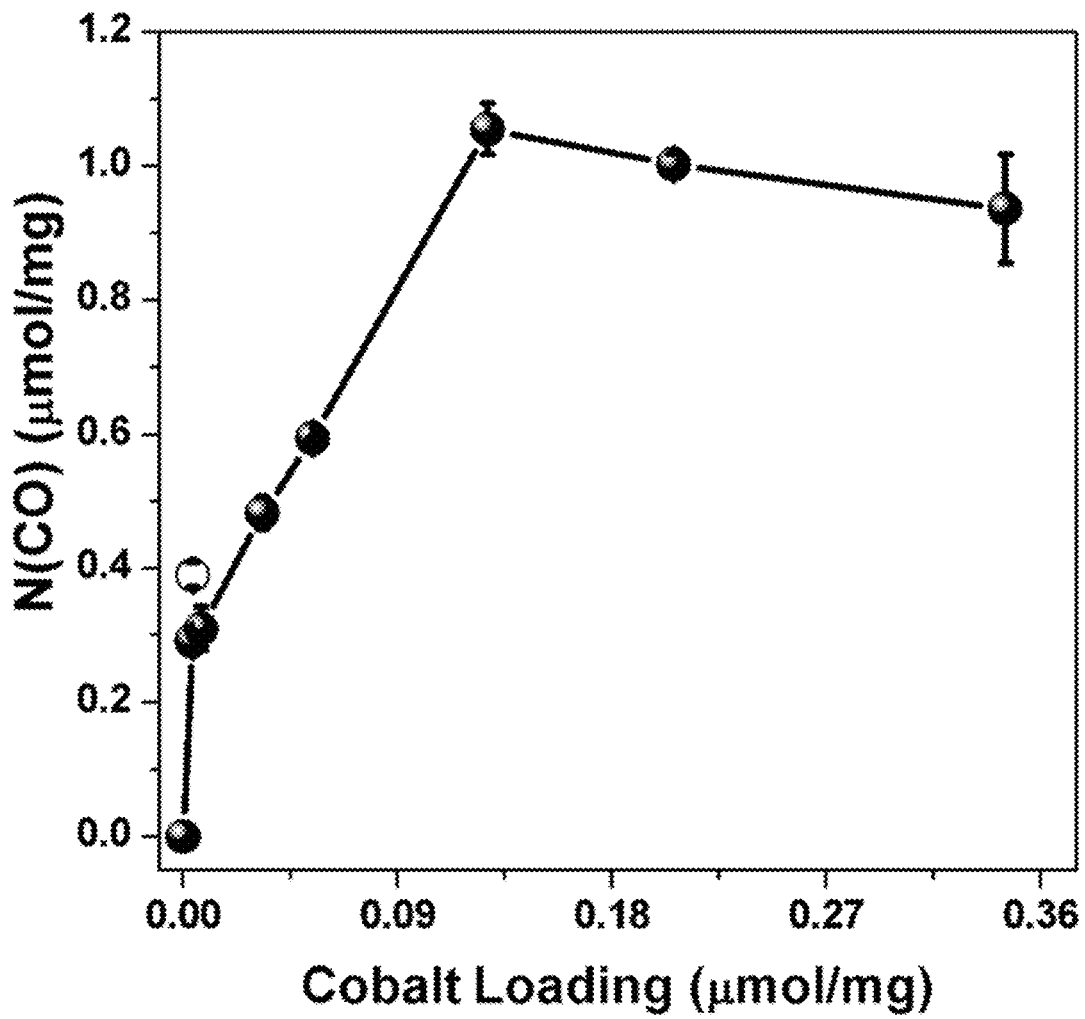
FIG. 16 illustrates the amounts of CO produced after $CO_2$ reduction for 2 h using $Co^{2+}$—$C_3N_4$ with different amounts of cobalt loadings.

FIG. 15 shows amounts of CO produced in different experimental conditions by using: (a) 1 mg $Co^{2+}$—$C_3N_4$ with a cobalt loading of 0.054 μmol/mg of $Co^{2+}$—$C_3N_4$; (b) a dispersion of 1 mg $C_3N_4$ in 0.054 μmol $CoCl_2$; and (c) 1 mg bare $C_3N_4$. In all three conditions, light intensity of 200 mW/cm² was applied for two hours. Negligible CO production was observed using bare $C_3N_4$. $CO_2$ reduction using a dispersion of $CoCl_2$ and $C_3N_4$ also generated significant amount of CO. However, $Co^{2+}$—$C_3N_4$ complex produced five times more CO at the same cobalt loading compared to the dispersion of $CoCl_2$ and $C_3N_4$. This highlights the importance of cobalt loading processes, in which Co—N coordination likely occurred, in activating the $Co^{2+}$ sites on $C_3N_4$.

The effect of cobalt loading on the photocatalytic activity of $Co^{2+}$—$C_3N_4$ was also examined under the same experimental conditions. FIG. 16 shows amounts of CO produced when amounts of cobalt loadings in $Co^{2+}$—$C_3N_4$ were varied. Results show significant CO production even at cobalt loadings lower than 0.010 μmol/mg of $Co^{2+}$—$C_3N_4$. The amount of CO generated in $CO_2$ reduction increased linearly with cobalt loading until it reached 0.128 μmol/mg.

Further increase in cobalt content beyond 0.128 μmol/mg resulted in a slight decrease in the amount of CO produced.

Quantum Yields and the Effects of Cobalt Loading on Quantum Yields

Quantum yields for photocatalytic $CO_2$ reduction were estimated based on the amounts of CO produced and the amounts of photons absorbed by the reaction solutions. The change in light intensity at 400 nm was measured after passing through a reaction solution with a cross section area of 4.95 cm$^2$. The following equation was used to calculate quantum yields because $CO_2$-to-CO conversion is a two-electron process, Quantum Yield=$2n(CO)/n(photon)$ where n(CO) and n(photon) are the amounts of CO molecules produced and the number of photons absorbed, respectively.

Table 1 shows quantum yields for CO production after $CO_2$ reduction for 2 h using 1 mg $Co^{2+}$—$C_3N_4$ with different cobalt loadings prepared in absence or presence of TEA. Light intensity was applied at 200 mW/cm$^2$.

|  | Co loading (μmol/mg) | CO produced (μmol) | Quantum yield (%) |
|---|---|---|---|
| No TEA | 0.004 | 0.390 | 0.031 |
| Samples prepared | 0.004 | 0.292 | 0.023 |
| in the presence | 0.008 | 0.310 | 0.025 |
| of TEA | 0.033 | 0.482 | 0.039 |
|  | 0.054 | 0.595 | 0.048 |
|  | 0.128 | 1.056 | 0.084 |
|  | 0.206 | 1.002 | 0.081 |
|  | 0.345 | 0.936 | 0.075 |

The quantum yield was further optimized by varying the amounts of $Co^{2+}$—$C_3N_4$ used as well as by varying the light intensity applied in photocatalysis using $Co^{2+}$—$C_3N_4$ with a cobalt loading of 0.128 μmol/mg. Table 2 shows optimized quantum yields for CO production by reducing $CO_2$ for 2 h using $Co^{2+}$—$C_3N_4$ with a cobalt loading of 0.128 μmol/mg.

| Photocatalyst Mass (mg) | Light Intensity (mW/cm$^2$) | Quantum Yield (%) |
|---|---|---|
| 1 | 200 | 0.08 |
| 4 | 100 | 0.25 |
| 10 | 60 | 0.40 |
| 20 | 20 | 0.17 |

Quantum yields up to 0.40% were obtained for CO production using the synthesized materials.

Turnover Numbers and the Effects of Cobalt Loading on Turnover Numbers

The effect of cobalt loading on the photocatalytic activity of $Co^{2+}$—$C_3N_4$ was also investigated by comparing turnover numbers (TONs) which were calculated based on the amount of product and the amount of cobalt present in the reaction suspension.

Figure 17A:
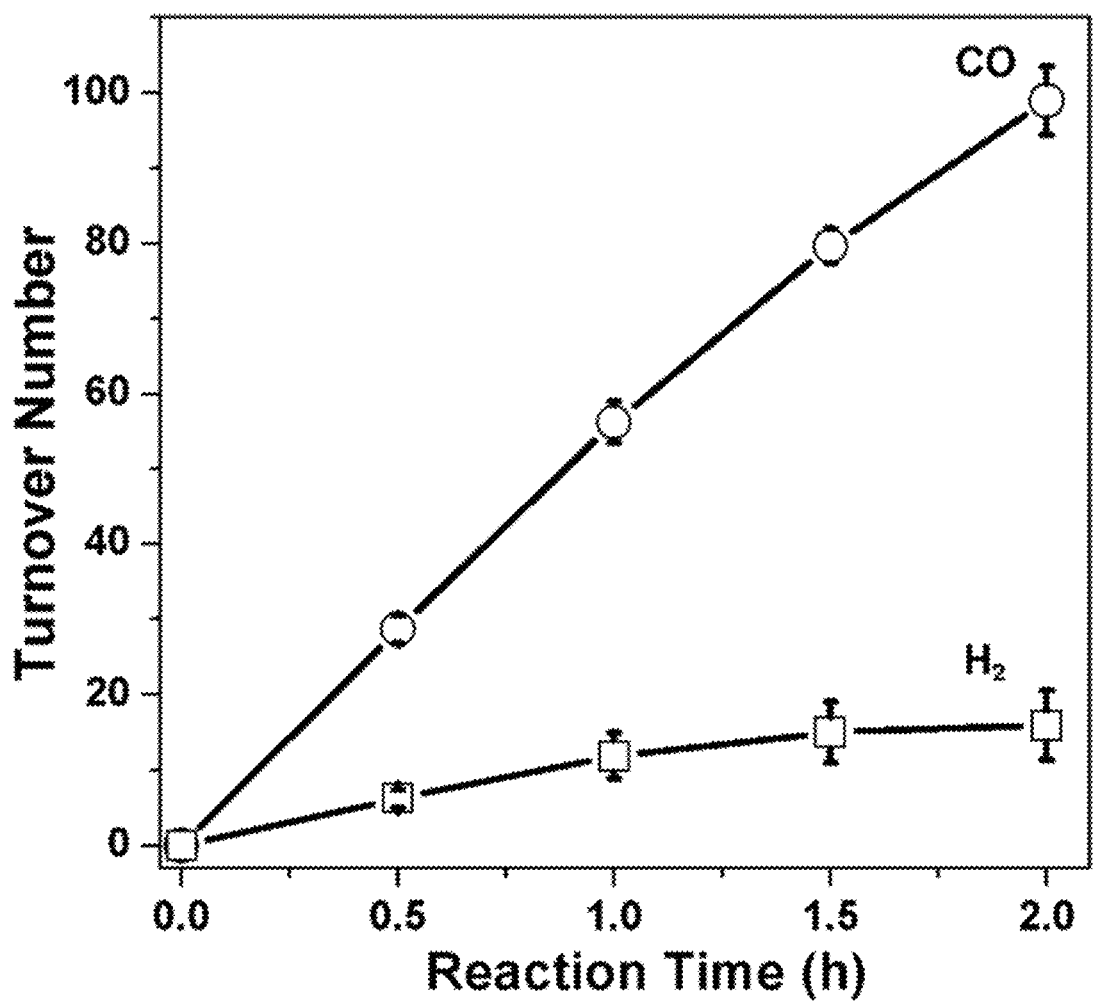
FIG. 17A illustrates turnover numbers (TONs) for CO and $H_2$ produced as a function of reaction time by a $Co^{2+}$—$C_3N_4$ sample.
Figure 17B:
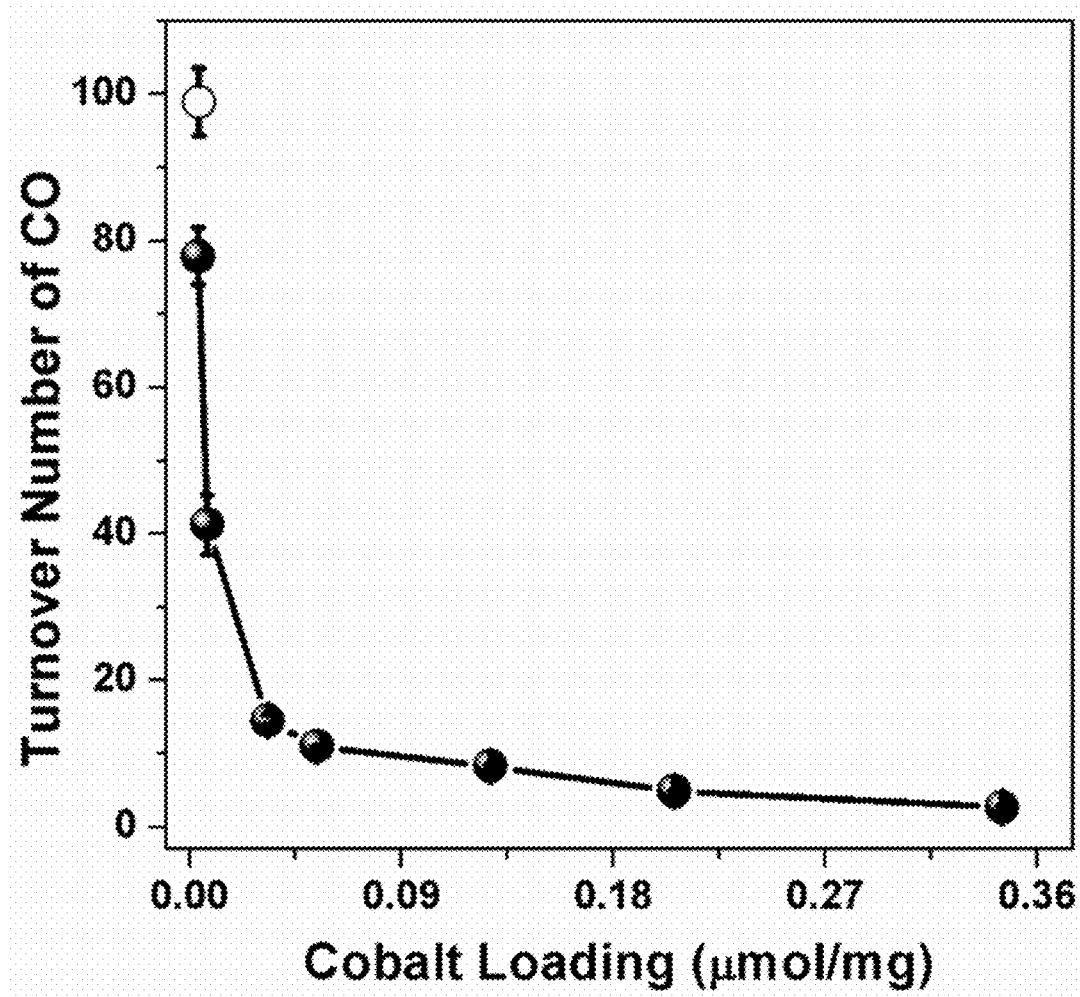
FIG. 17B illustrates TONs of CO production after $CO_2$ reduction for 2 h using $Co^{2+}$—$C_3N_4$ with different amounts of cobalt loadings. The open cycle represents a $Co^{2+}$—$C_3N_4$ sample prepared in the absence of TEA. Close cycles represent $Co^{2+}$—$C_3N_4$ samples prepared in presence of TEA.

FIG. 17A shows turnover numbers for CO and $H_2$ production as a function of reaction time using a $Co^{2+}$—$C_3N_4$ sample prepared in the absence of TEA. Results show that TON for CO formation, after reducing $CO_2$ for 2 h, is about 100. FIG. 17B, however, shows that TONs for CO formation drastically decreased when the cobalt loading was increased. This indicates the existence of single site catalysis at low cobalt loading. At higher cobalt loading, a significant portion of cobalt likely exists in the form of inactive cobalt oxides which do not contribute to catalytic reduction of $CO_2$.

Figure 18:
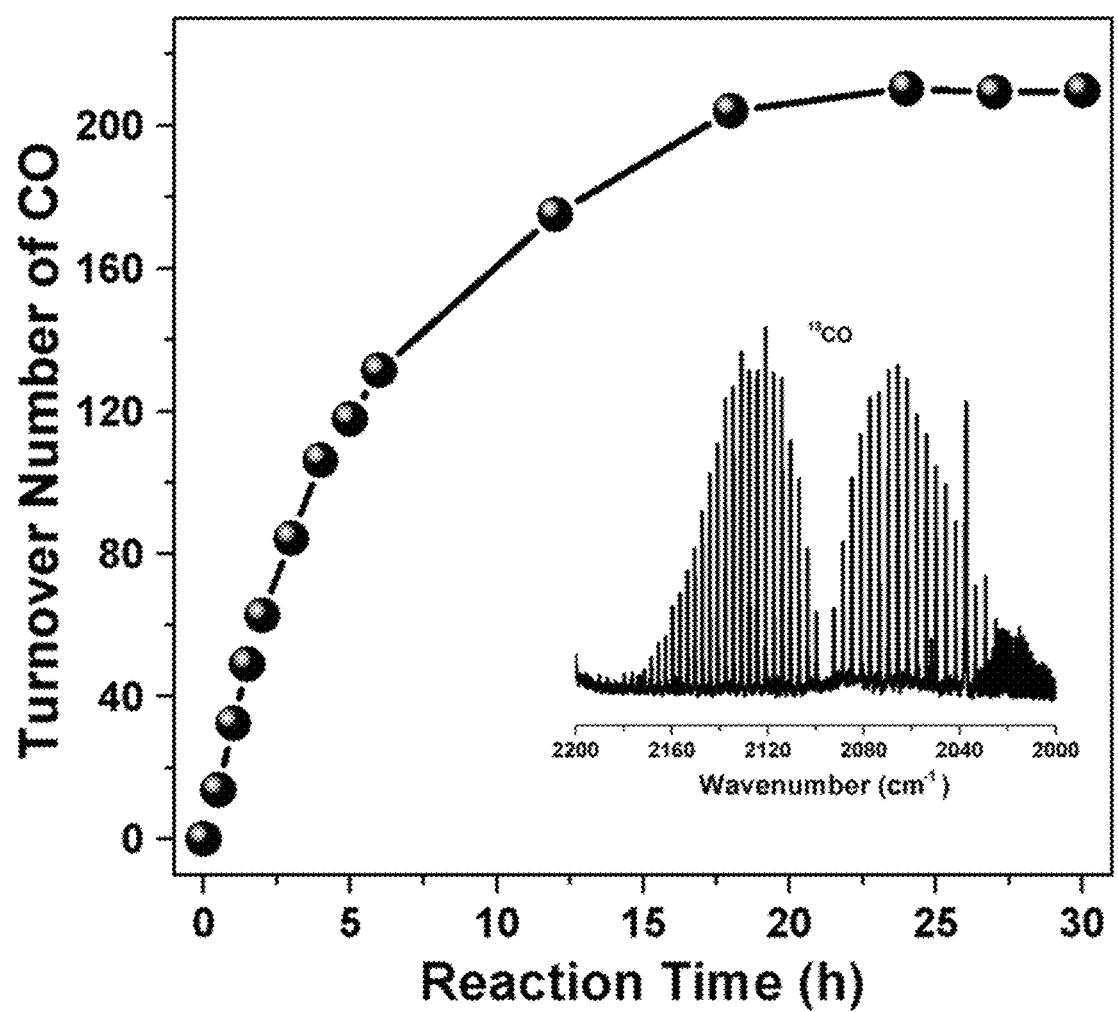
FIG. 18 illustrates TONs of CO produced by $CO_2$ reduction under visible-light irradiation (λ>420 nm, light intensity 200 mW/cm$^2$) using 1 mg $Co^{2+}$—$C_3N_4$ with a cobalt loading of 0.004 μmol/mg prepared in the absence of TEA. The insert illustrates the infrared spectrum of gaseous $^{13}CO$ produced in the reduction of $^{13}CO_2$.

The $Co^{2+}$—$C_3N_4$ samples demonstrated excellent activity under visible-light irradiation (λ>420 nm). FIG. 18 shows that a TON greater than 200 was obtained after $CO_2$ reduction for 24 h using a $Co^{2+}$—$C_3N_4$ sample. Isotopic studies, as shown by the insert in FIG. 18, clearly show that CO was produced as a result of $CO_2$ reduction, and that CO was not generated from any other source.

Figure 19:
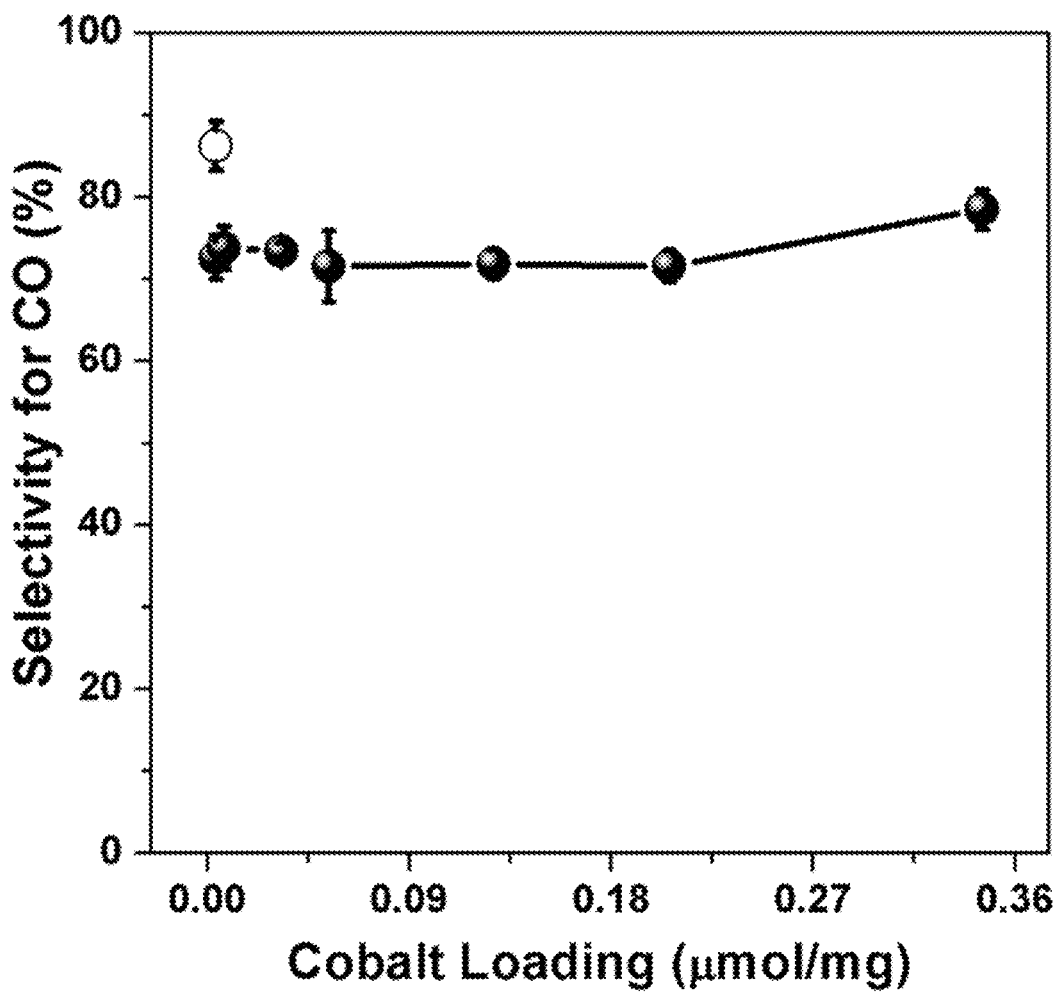
FIG. 19 illustrates selectivity of $Co^{2+}$—$C_3N_4$ with different amounts of cobalt loadings toward CO production after $CO_2$ reduction for 2 h. The open cycle represents a $Co^{2+}$—$C_3N_4$ sample prepared in the absence of TEA. Close cycles represent $Co^{2+}$—$C_3N_4$ samples prepared in presence of TEA.

Photocatalytic $CO_2$ reduction using $Co^{2+}$—$C_3N_4$ is quite selective towards CO production. FIG. 19 shows the percentage selectivity of $Co^{2+}$—$C_3N_4$ catalyst for CO formation, and the product selectivity for CO formation remained independent of cobalt loading. That is, even at higher cobalt loading in $Co^{2+}$—$C_3N_4$, the percentage selectivity for CO remain unchanged. This suggests that the inactive cobalt, may be deposited in the form of cobalt oxides at higher cobalt loading, does not take part or promote undesirable product formations. The open circle in FIG. 19 represents the $Co^{2+}$—$C_3N_4$ formed in absence of TEA. Closed circles in FIG. 19 represent the $Co^{2+}$—$C_3N_4$ formed in presence of TEA.

Stability of $Co^{2+}$—$C_3N_4$

Figure 20:
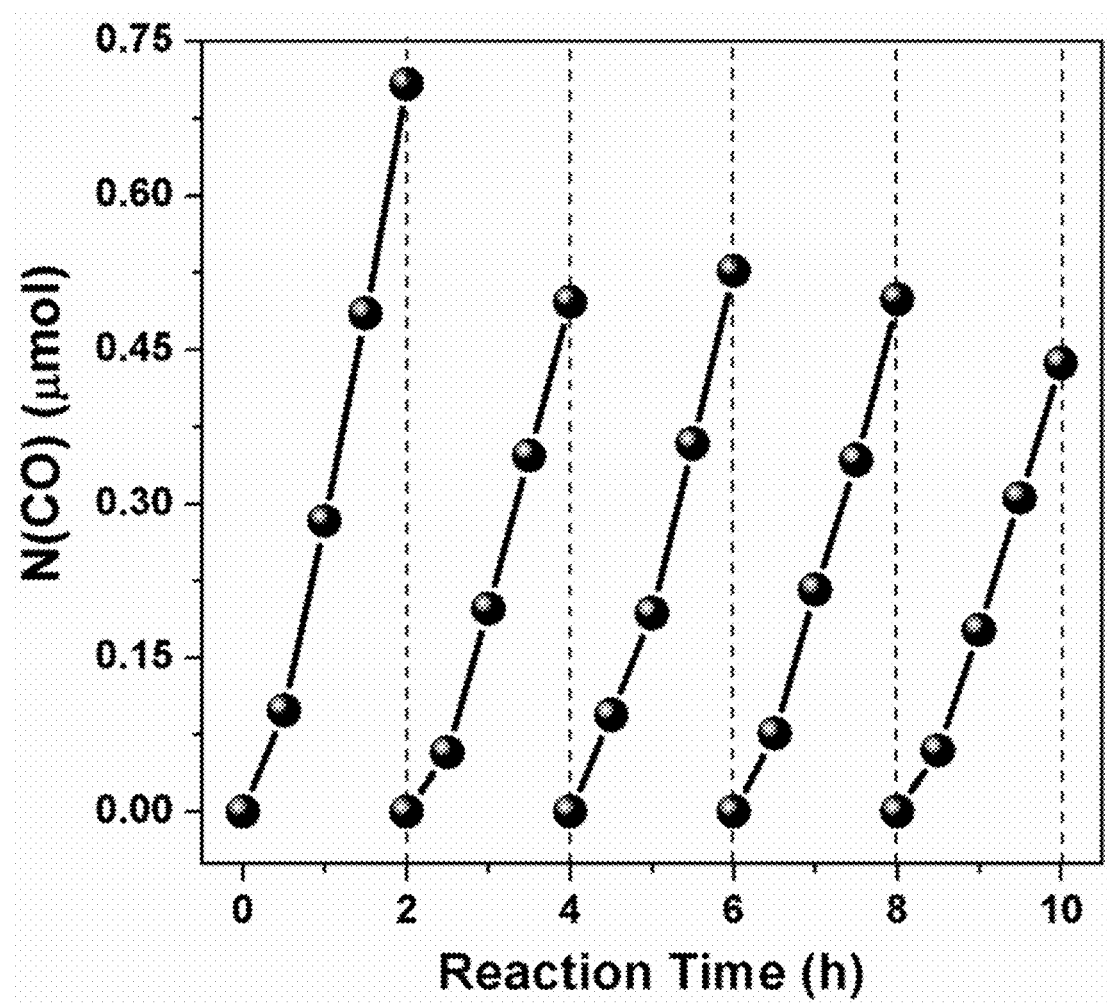
FIG. 20 illustrates CO production upon $CO_2$ reduction for five 2-hour cycles using 10 mg $Co^{2+}$—$C_3N_4$ with a cobalt loading of 0.128 μmol/mg in 4.0 mL acetonitrile containing triethanolamine (TEOA) (light intensity 60 mW/cm$^2$).

The stability of $Co^{2+}$—$C_3N_4$ was also demonstrated as indicated by significant CO production using reused $Co^{2+}$—$C_3N_4$ in FIG. 20. In order to test the reusability of $Co^{2+}$—$C_3N_4$, 10 mg of $Co^{2+}$—$C_3N_4$ with cobalt loading of 0.128 μmol/mg was dispersed in 4.0 mL of acetonitrile containing TEOA and irradiated with light intensity of 60 mW/cm$^2$ for 2 h (λ>350 nm). The resultant CO amount produced was recorded. After 2 h, the photocatalyst $Co^{2+}$—$C_3N_4$ was collected by centrifugation, and rinsed with acetonitrile, and then was redispersed in a fresh 4.0 mL of acetonitrile containing TEOA. The photocatalysis was then repeated under the same conditions after purging with $CO_2$. FIG. 20 shows five cycles of photocatalysis using same $Co^{2+}$—$C_3N_4$ sample where each cycle of catalysis lasted for two hours. It is interesting to note that $Co^{2+}$—$C_3N_4$ is able to maintain its catalytic efficiency even after 5 cycles.

Figures 21A, 21B:
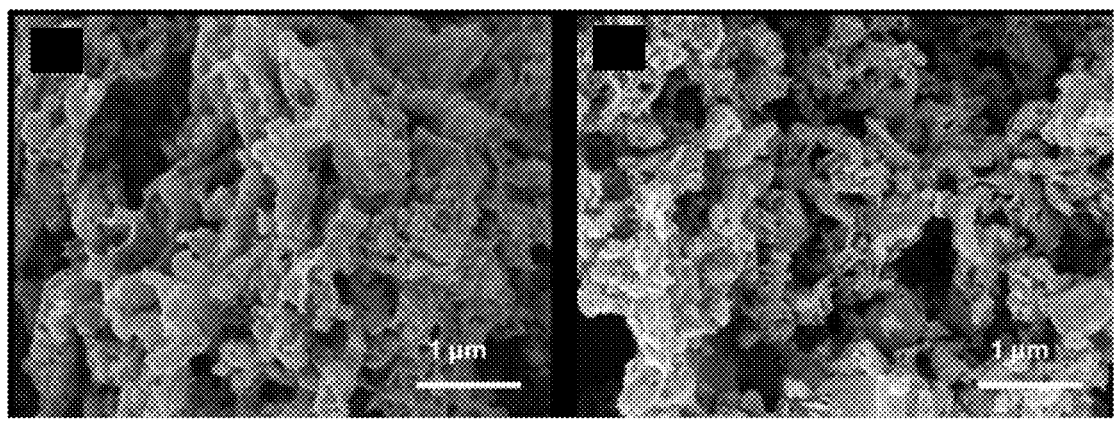
FIG. 21A-B illustrate SEM images of $Co^{2+}$—$C_3N_4$ with a cobalt loading of 0.004 μmol/mg.
Figures 21C, 21D:
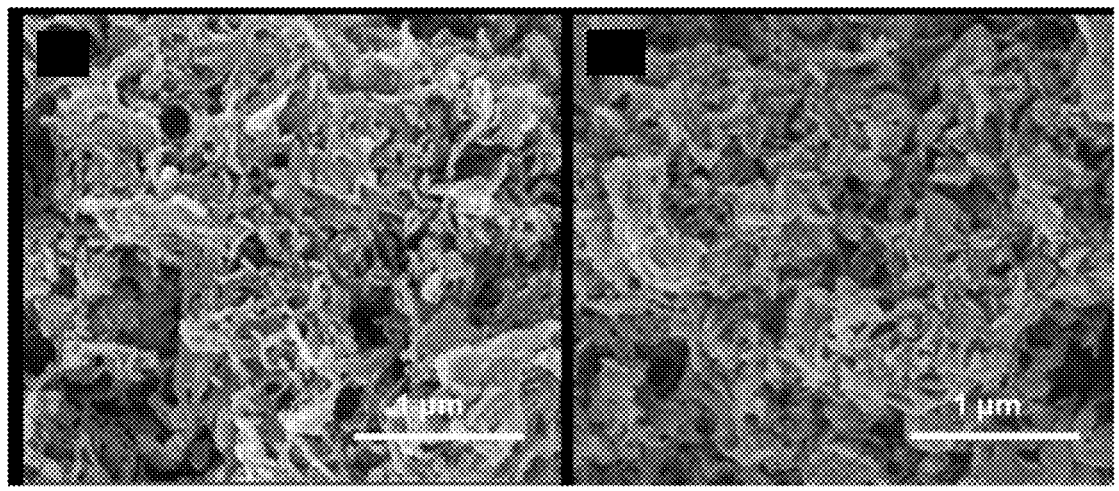
FIG. 21C-D illustrate SEM images of $Co^{2+}$—$C_3N_4$ with a cobalt loading of 0.128 μmol/mg.

In addition to maintaining photocatalytic ability, $Co^{2+}$—$C_3N_4$ did not exhibit any measured morphological changes after photocatalysis as shown in FIGS. 21A-B. FIG. 21A-B show SEM images of $Co^{2+}$—$C_3N_4$ with a cobalt loading of 0.004 μmol/mg: (a) before and (b) after photocatalysis for 30 h. No morphological changes were observed in $Co^{2+}$—$C_3N_4$ even after 30 h of photocatalysis. FIGS. 21C-D provide SEM images of $Co^{2+}$—$C_3N_4$ with a cobalt loading of 0.128 mol/mg: (a) before and (b) after photocatalysis for five 2-hour cycles. Even after 5 cycles of photocatalysis, no morphological changes were observed in $Co^{2+}$—$C_3N_4$. This confirms the photocatalytic and structural stability of $Co^{2+}$—$C_3N_4$.

Confirmation of Model Having Metal Coordination at Edge Sites

Figure 22:
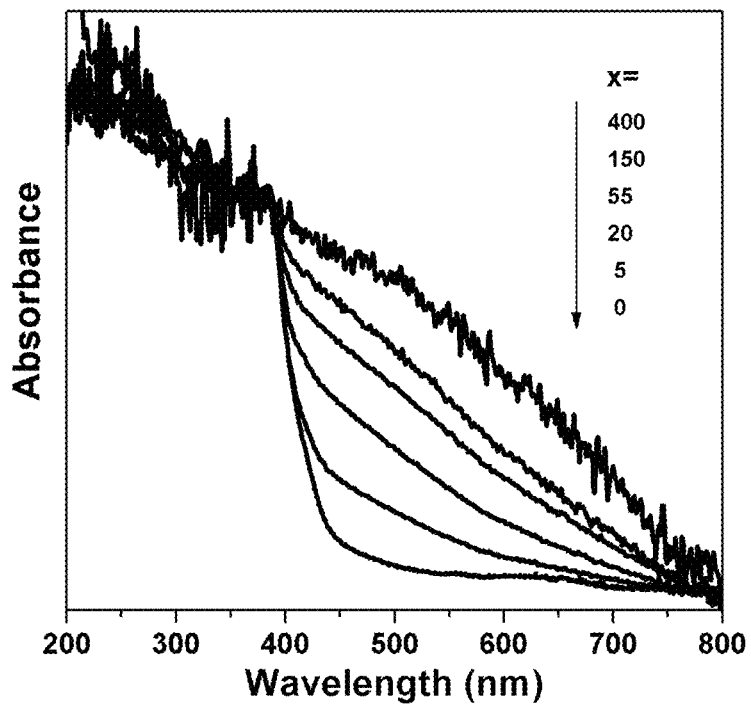
FIG. 22 illustrates UV-vis spectra of various C-doped $C_3N_4$ samples, "C(x)—$C_3N_4$", with x=0, 5, 20, 55, 150 and 400 from bottom to top.

Experiments were performed to confirm that metal-N coordination is responsible for $CO_2$-reduction activity using metal coordinated at edge sites of the model. $C(x)$—$C_3N_4$ materials with different amount of doped C were synthesized (with x=0, 5, 20, 55, 150, and 400 mg) and characterized with different techniques including UV-vis. The samples were synthesized from 99.6% urea and a small amount of dextrose as a carbon source. FIG. 22 illustrates the UV-vis spectra from 200 nm to 800 nm for each of the prepared samples. Increased absorbance in the visible spectra was observed for increased amounts of doped carbon.

Figure 23:
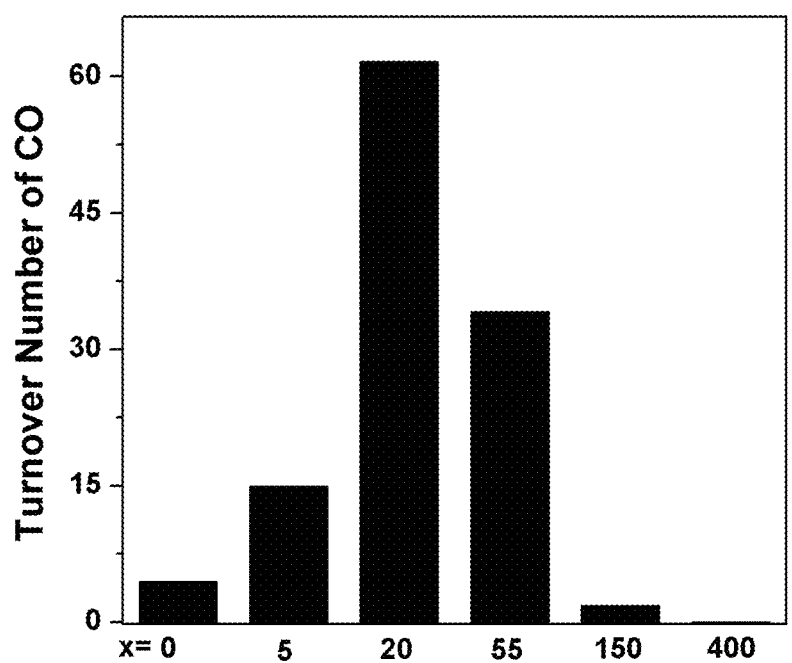
FIG. 23 illustrates TONs for CO produced after photocatalytic $CO_2$ reduction for 2 hours using $Co^{2+}$ on C(x)—$C_3N_4$ samples with x=0, 5, 20, 55, 150, and 400 from left to right.

The $C(x)$—$C_3N_4$ materials containing single $Co^{2+}$ sites were tested in a photocatalytic $CO_2$ reduction. The photocatalysis conditions include 1 mg photocatalyst in 4.0 mL acetonitrile containing triethanolamine with a light intensity of 200 mW/cm$^2$. The sample $Co^{2+}$ on $C(20)$—$C_3N_4$ (e.g., x=20) demonstrated the best activity among these materials as shown in FIG. 23.

Figure 24:
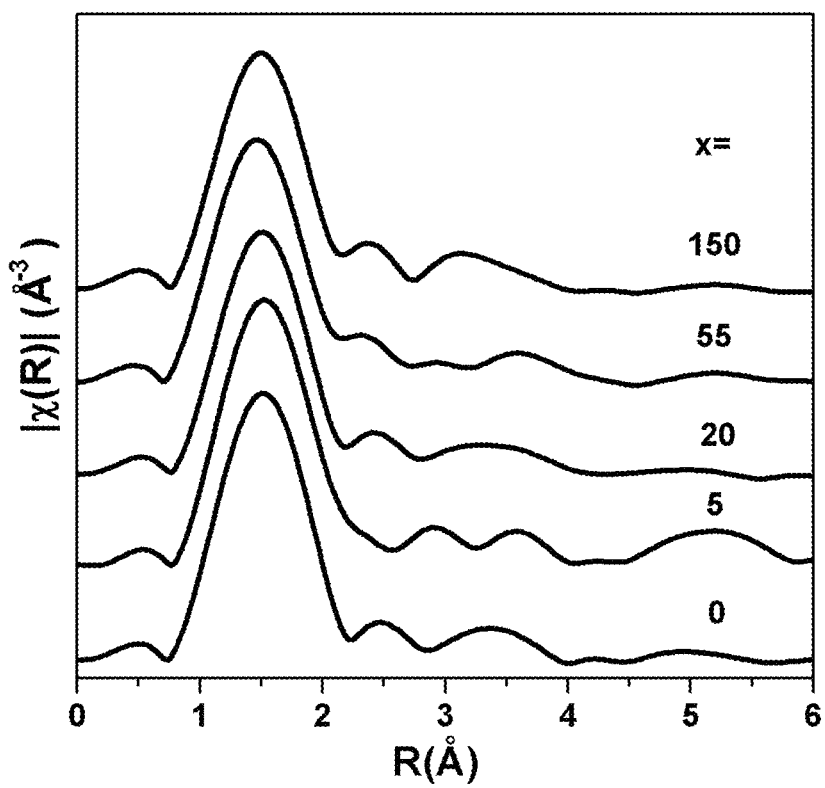
FIG. 24 illustrates Fourier transform magnitude of $k^2$-weighted Co K-edge EXAFS spectra of $Co^{2+}$ on C(x)—$C_3N_4$ samples with x=0, 5, 20, 55, and 150 from bottom to top.

The samples with $CO_2$-reduction activity were further characterized with EXAFS spectroscopy to confirm the presence of single $Co^{2+}$ sites (peak absorption observed around 1.5 Å) as shown in FIG. 24. Together with activity, additional results obtained through analyzing EXAFS data support that the active $Co^{n+}$ centers exist at edge sites on the $C_3N_4$ support. Table 3 below shows activity and EXAFS spectra fitting results for $Co^{2+}$ on $C(0)$—$C_3N_4$ and $C(20)$—$C_3N_4$. Treatment with $NH_3$ was utilized to create more edge sites for $Co^{2+}$ coordination. A TON for CO production of more than 800 was obtained after photocatalytic $CO_2$ reduction for 2 h using $C^{2+}$ on $NH_3$-treated $C(20)$—$C_3N_4$.

|  | Sample | TON $^a$ | $d_{Co-N}$ $^b$ | CN $^c$ |
|---|---|---|---|---|
| Without $NH_3$ treatment | $Co^{2+}$ on $C(0)$—$C_3N_4$ | 4.4 | 2.08 ± 0.02 | 4.2 ± 0.9 |
|  | $Co^{2+}$ on $C(20)$—$C_3N_4$ | 61.6 | 2.08 ± 0.02 | 4.2 ± 1.1 |
| With $NH_3$ treatment | $Co^{2+}$ on $C(0)$—$C_3N_4$ | 7.9 | 2.09 ± 0.02 | 4.5 ± 1.1 |
|  | $Co^{2+}$ on $C(20)$—$C_3N_4$ | 818.9 | 2.03 ± 0.05 | 4.2 ± 2.3 |

$^a$ Turnover numbers for CO production after $CO_2$ reduction for 2 hours;
$^b$ Co—N distance in angstrom;
$^c$ Co—N coordination number.

Figure 25:
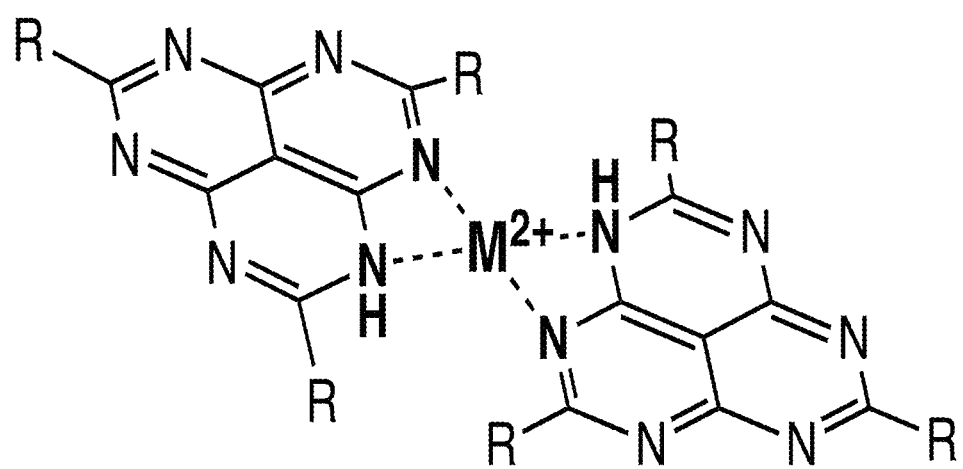
FIG. 25 illustrates a structure of potential molecular catalysts for $CO_2$ reduction where R=H or $NH_2$ and $M^{2+}=Co^{2+}$ or $Ni^{2+}$.

Based at least on these results, FIG. 25 illustrates a functional model of molecular catalysts that would be highly active in $CO_2$-reduction catalysis, where R=H or $NH_2$ and $M^{2+}$=$Co^{2+}$ or $Ni^{2+}$.

What is claimed is:

1. A photocatalyst comprising:
    graphitic carbon nitride flakes providing nitrogen atoms for direct coordination with a transition metal ion in absence of additional ligands, the transition metal ion forming four coordinate bonds with the nitrogen atoms at edge sites of the graphitic carbon nitride flakes, two of the coordinate bonds with nitrogen atoms on an edge site of a first flake and two of the coordinate bonds with nitrogen atoms on an edge site of a second flake.

2. The photocatalyst of claim 1, wherein the transition metal ion is $Co^{2+}$.

3. The photocatalyst of claim 2, wherein $Co^{2+}$ is at a concentration between 0.004 and 0.430 μmol/mg of the photocatalyst.

4. The photocatalyst of claim 2, wherein $Co^{2+}$ is atomically dispersed on the graphitic carbon nitride flakes.

5. The photocatalyst of claim 2, wherein a molar ratio of $Co^{2+}$ to cobalt oxide in the photocatalyst is greater than 1000.

6. The photocatalyst of claim 1, wherein the graphitic carbon nitride flakes are planar.

7. The photocatalyst of claim 1, wherein the graphitic carbon nitride flakes include carbon doping.

8. The photocatalyst of claim 1, wherein the transition metal ion is positioned outside a plane formed by the nitrogen atoms by a distance less than 0.5 Angstrom.

9. The photocatalyst of claim 1, wherein the transition metal ion forms coordinate bonds with four nitrogen atoms at edge sites of the graphitic carbon nitride flakes.

10. The photocatalyst of claim 1, comprising a transition metal selected from Ni, Fe, Cu, Pt, Pd, and Co.

* * * * *